United States Patent [19]

Gerson et al.

[11] Patent Number: 4,797,929
[45] Date of Patent: Jan. 10, 1989

[54] WORD RECOGNITION IN A SPEECH RECOGNITION SYSTEM USING DATA REDUCED WORD TEMPLATES

[75] Inventors: Ira A. Gerson, Hoffman Estates; Brett L. Lindsley; Philip J. Smanski, both of Palatine, all of Ill.

[73] Assignee: Motorola, Inc., Schaumburg, Ill.

[21] Appl. No.: 816,161

[22] Filed: Jan. 3, 1986

[51] Int. Cl.$^4$ ............................................. G10L 5/00
[52] U.S. Cl. ..................................................... 381/43
[58] Field of Search ........................................ 381/43

[56] References Cited

U.S. PATENT DOCUMENTS

| | | | |
|---|---|---|---|
| 3,582,559 | 6/1971 | Hitchcock et al. | 381/43 |
| 3,812,291 | 5/1974 | Brodes et al. | 381/43 |
| 4,132,867 | 9/1977 | Siglow . | |
| 4,181,813 | 1/1980 | Marley . | |
| 4,227,176 | 10/1980 | Moshier . | |
| 4,227,177 | 10/1980 | Moshier . | |
| 4,412,098 | 10/1983 | An | 381/43 |
| 4,415,767 | 11/1983 | Gill et al. . | |
| 4,449,190 | 5/1984 | Flanagan et al. . | |
| 4,449,233 | 3/1982 | Brantingham . | |
| 4,489,434 | 12/1984 | Moshier . | |
| 4,489,435 | 12/1984 | Moshier . | |
| 4,513,436 | 4/1985 | Nose et al. . | |

OTHER PUBLICATIONS

"The Effects of Selected Signal Processing Techniques on the Performance of a Filter Bank Based Isolated Word Recognizer", B. A. Dautrich, L. R. Rabiner, and T. B. Martin, Bell System Technical Journal, vol. 62, No. 5, (May-Jun. 1983), pp. 1311-1335.
"An Algorithm for Connected Word Recognition" IEEE International Conference on Acoustics, Speech, and Signal Processing, May 3-5, 1982, vol. 2, pp. 899-902.
"A Real-Time Hardware Continous Speech Recognition System", IEEE International Conference on Acoustics, Speech, and Signal Processing, (May 3-5 1982), vol. 2, pp. 863-866.
"The Harpy Speech Recognition System" Ph.D. Dissertation, Computer Science Dept., Carnegie-Mellon University 1977.
"Minimum Prediction Residual Principle Applied to Speech Recognition", IEEE Trans. Acoustics, Speech and Signal Processing, vol. ASSP-23, pp. 67-72.
"Systoloic Arrays for Dynamic Programming in S.R.S.", J. MacAllister, IEEE 1983, ICASSP 83, Boston.
"Segmentation for Data Reduction in Isolated Word Recognition", R. W. Brown, International Conference-ASSP, 1982, pp. 1262-1265.
"LPC Speech at 1200 bps Using Optimized Frame Repeat", G. Helms, Acoustical Society of America and Acoustical Society of Japan Joint Meeting, Dec. 1978, pp. 5159-5160.
"Memory and Time Improvements in a Dynamic Programming Algorithm for Matching Speech Patterns", by C. C. Tappert and Subrata K. Das, IEEE 0096-3518/78/1200-0583.

Primary Examiner—Emanuel S. Kemeny
Attorney, Agent, or Firm—Robert J. Crawford

[57] ABSTRACT

Described herein, is an arrangement and method for processing speech information in a speech recognition system (300). In such a system where the speech information is depicted as words, each word representing a sequence of frames (510) and where the recognition system has means (120) for comparing present input speech to a word template, the word template stored in template memory and derived from one or more previous input word, the present invention is best employed. The invention describes combining contiguous acoustically similar frames (512) derived from the previous input word or words into representative frames to form a corresponding reduced word template, storing the reduced word template in template memory in an efficient manner, and comparing frames of the present input speech to the representative frames of the reduced word template according to the number of frames combined in the representative frames of the reduced word template. In doing so, a measure of similarity between the present input speech and the word template is generated.

29 Claims, 25 Drawing Sheets

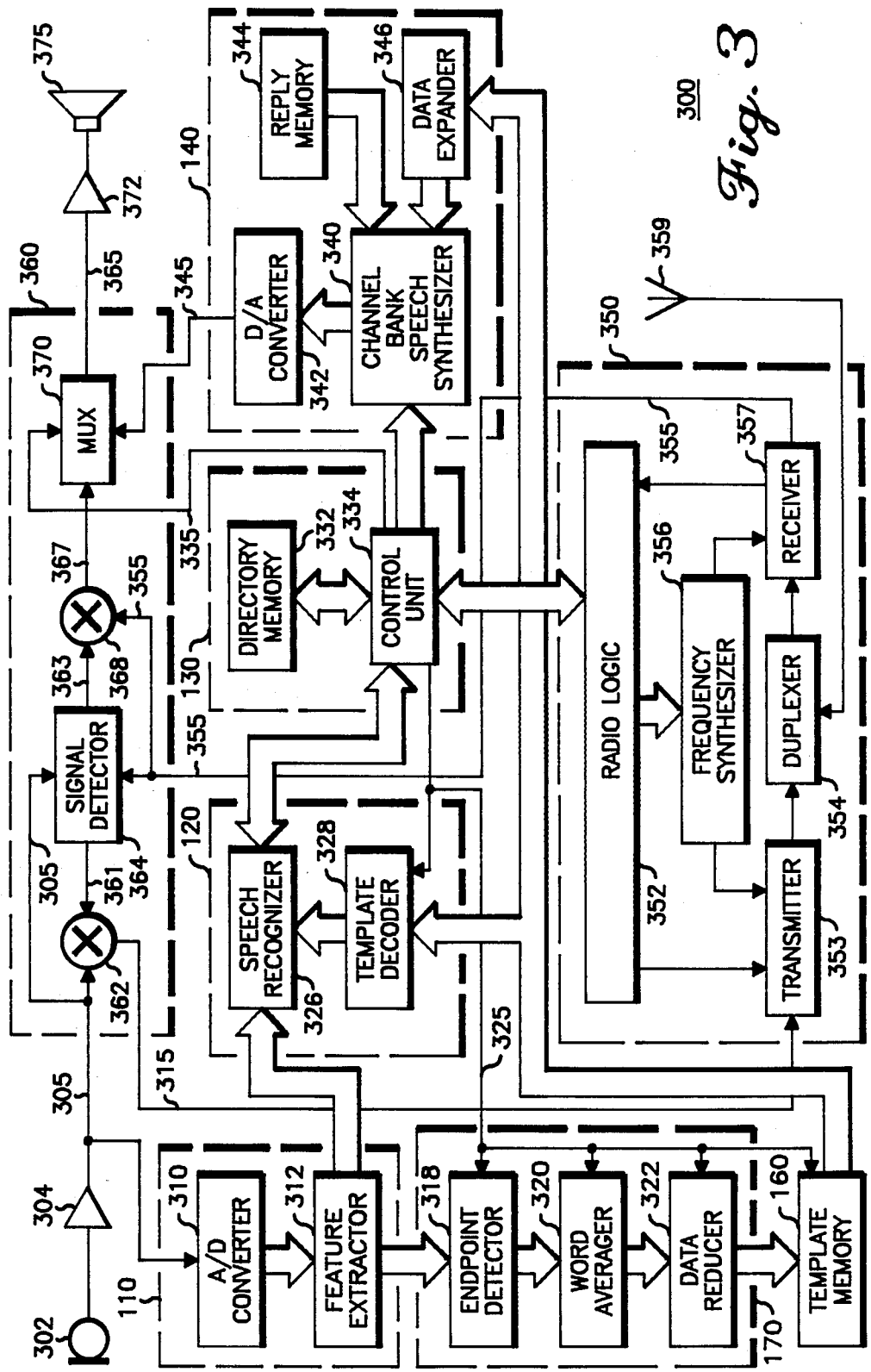

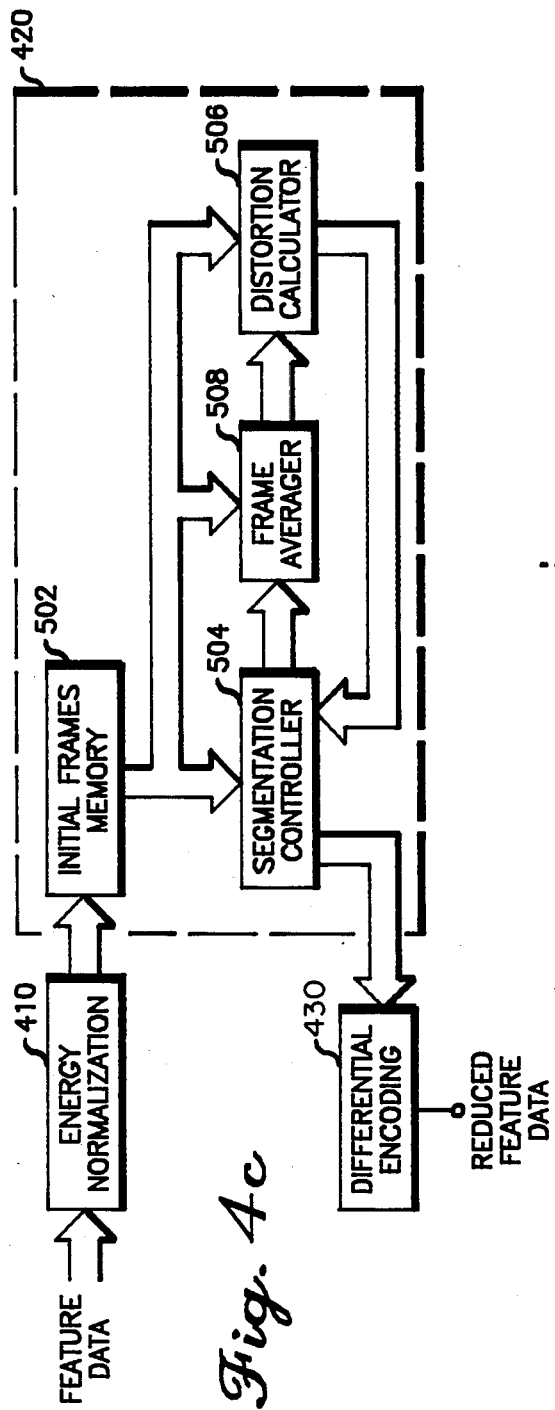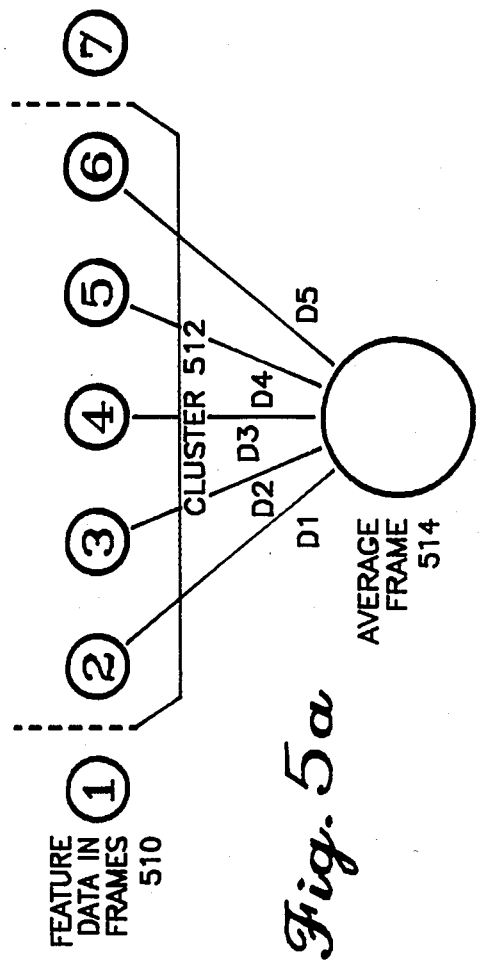

Fig. 5b $Y1 = Y_o + C0,1$ $Y2 = MIN \{ Y_o+C0,2; Y1+C1,2 \}$ $Y3 = MIN \{ Y_o+C0,3; Y1+C1,3; Y2+C2,3 \}$ $Y4 = MIN \{ Y_o+C0,4; Y1+C1,4; Y2+C2,4; Y3+C3,4 \}$

Y1: ①―520

Y2: $\overset{x}{①}$②―522  OR  ①②―524

Y3: $\overset{x}{①}$②③―526  OR  ①②③―528
        $\overset{x}{①}$②③―530
        $\overset{xx}{①}$②③―532

Y4: $\overset{x}{①}$②③④―534  OR  ①②③④―536
        $\overset{x}{①}$②③④―538
        ①②③④―540
        $\overset{x}{①}$②③④―542
        ①②③④―544
        $\overset{xx}{①}$②③④―546
        $\overset{x}{①}$②③④―548

TRACKBACK POINTERS
| FRAME No. | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|---|
| POINTER | NULL | — | 0 | 0 | 0 | 1 | 3 | 4 | 4 | 5 | 7 | 8 | 10 | 9 | 10 | 12 | 12 | 14 | 15 | 16 | 19 | 17 | 18 | 20 |
*Fig. 5g*
FRAME CONNECTION TREE
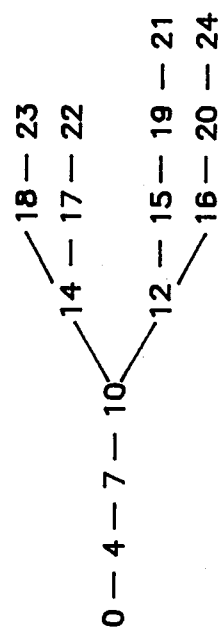
*Fig. 5h*
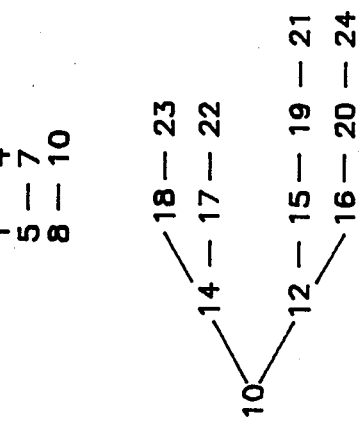
*Fig. 5i*

430

REDUCED DATA FORMAT

FLOWCHART FOR WORD MODEL DECODER

STATE DECODER FLOWCHART

742

WORD RECOGNITION IN A SPEECH RECOGNITION SYSTEM USING DATA REDUCED WORD TEMPLATES

BACKGROUND

The present invention relates to word recognition for a speech recognition system and, more particularly, to word recognition using word templates having a data reduced format.

Typically, speech recognition systems represent spoken words as word templates stored in system memory. When a system user speaks into the system, the system must digitally represent the speech for comparison to the word templates stored in memory.

Two particular aspects of such an implementation have received a great deal of attention. The first aspect pertains to the amount of memory which is required to store the word templates. The representation of speech is such that the data used for matching to an input word typically requires a significant amount of memory to be dedicated for each particular word. Moreover, a large vocabulary causes extensive computation time to be consumed for the match. In general, the computation time increases linearly with amount of memory required for the template memory. Practical implementation in real time requires that this computation time be reduced. Of course, a faster processor architecture could be employed to reduce this computation time, but due to cost considerations, it is prefered that the data representing the word templates be reduced to reduce the computation.

The second aspect pertains to the particular matching techniques used in the system. Most word recognition techniques have been directed to the accuracy of the recognition process for a particular type of feature data used to represent the speech. Typically, channel bank information or LPC parameters represent the speech. When using feature data of a reduced format, the word recognition process must be sensitive to the format for an effective implementation.

The speech recognition system, described herein, clusters frames within the word templates to reduce the representative data, for which a word recognition technique requires special consideration to the combined frames. Data reduced word templates represent spoken words in a compacted form. Matching an incoming word to a reduced word template without adequately compensating for its compacted form will result in degraded recognizer performance. An obvious method for compensating for data reduced word templates would be uncompacting the reduced data before matching. Unfortunately, uncompacting the reduced data defeats the purpose of data reduction. Hence, a word recognition method is needed which allows reduced data to be directly matched against an incoming spoken word without degrading the word recognition process.

OBJECTS AND SUMMARY OF THE PRESENT INVENTION

Accordingly, an object of the present invention is to provide a system of word recognition which reduces template data and recognizes the reduced data in an efficient manner.

The present invention teaches an arrangement and method for processing speech information in a speech recognition system. In a system where the information is depicted as words, each word represented by sequence of frames and where the recognition system has means for comparing present input speech to a word template, the word template stored in template memory and derived from one or more previous input words, the processing method includes (1) combining continguous acoustically similar frames derived from the previous input word (3) into representative frames to form a corresponding reduced word template, (2) storing the reduced word template in template memory in an efficient manner, and (3) comparing frames of the present input speech to the representative frames of the reduced word template according to the number of frames combined in the representative frames of the reduced word template to produce a measure of similarity between the present input speech and the word template.

BRIEF DESCRIPTION OF THE DRAWINGS

Additional objects, features, and advantages in accordance with the present invention will be more clearly understood by reference to the following description taken in connection with the accompanying drawings, in the several figures of which like reference numerals identify like elements, and in which:

FIG. 3 is a detailed block diagram of the preferred embodiment of the present invention illustrating a radio transceiver having a hands-free speech recognition/speech synthesis control system;

FIG. 4b is a flowchart showing the sequence of steps performed by the energy normalization block 410 of FIG. 4a;

FIG. 4c is a detailed block diagram of the of the particular hardware configuration of the segmentation/compression block 420 of FIG. 4a;

FIG. 5a is a graphical representation of a spoken word segmented into frames for forming a cluster according to the present invention;

FIG. 5b is a diagram exemplifying output clusters being formed for a particular word template, according to the present invention;

FIGS. 5d and 5e show a flowchart illustrating a basic implementation of the data reduction process performed by the segmentation/compression block 420 of FIG. 4a;

FIG. 5g is a traceback pointer table illustrating a clustering path for 24 frames, according to the present invention, applicable to partial traceback;

FIG. 5h is a graphical representation of the traceback pointer table of FIG. 5g illustrated in the form of a frame connection tree;

FIG. 5i is a graphical representation of FIG. 5h showing the frame connection tree after three clusters have been output by tracing back to common frames in the tree;

FIGS. 6a and 6b comprise a flowchart showing the sequence of steps performed by the differential encoding block 430 of FIG. 4a;

FIG. 8b is a flowchart showing the sequence of steps performed by the differential decoding block 802 of FIG. 8a;

FIG. 8c is a flowchart showing the sequence of steps performed by the energy denormalization block 804 of FIG. 8a;

FIG. 8d is a flowchart showing the sequence of steps performed by the frame repeating block 806 of FIG. 8a;

FIG. 9b is an alternate embodiment of the modulator/bandpass filter configuration 980 of FIG. 9a;

FIG. 9c is a detailed block diagram of the preferred embodiment of the pitch pulse source 920 of FIG. 9a;

DESCRIPTION OF THE PREFERRED EMBODIMENT

1. System Configuration

Figure 1:
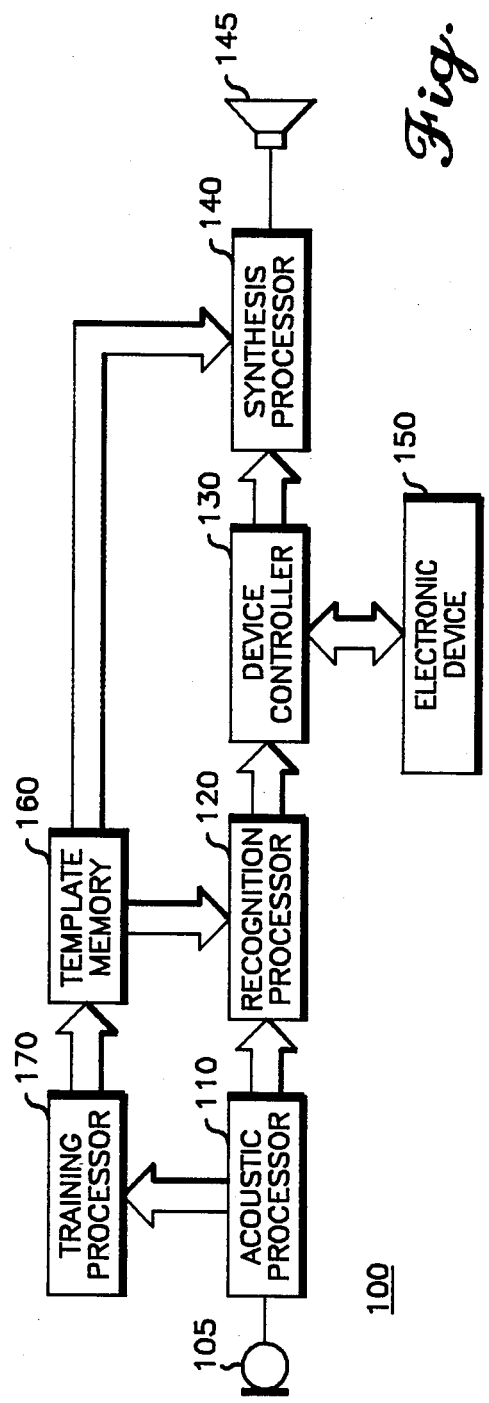
FIG. 1 is a general block diagram illustrating the technique of synthesizing speech from speech recognition templates according to the present invention.

Referring now to the accompanying drawings, FIG. 1 shows a general block diagram of user-interactive control system 100 of the present invention. Electronic device 150 may include any electronic apparatus that is sophisticated enough to warrant the incorporation of a speech recognition/speech synthesis control system. In the preferred embodiment, electronic device 150 represents a speech communications device such as a mobile radiotelephone.

User-spoken input speech is applied to microphone 105, which acts as an acoustic coupler providing an electrical input speech signal for the control system. Acoustic processor 110 performs acoustic feature extraction upon the input speech signal. Word features, defined as the amplitude/frequency parameters of each user-spoken input word, are thereby provided to speech recognition processor 120 and to training processor 170. Acoustic processor 110 may also include a signal conditioner, such as an analog-to-digital converter, to interface the input speech signal to the speech recognition control system. Acoustic processor 110 will be further described in conjunction with FIG. 3.

Training processor 170 manipulates this word feature information from acoustic processor 110 to provide word recognition templates to be stored in template memory 160. During the training procedure, the incoming word features are arranged into individual words by locating their endpoints. If the training procedure is designed to accommodate multiple training utterances for word feature consistency, then the multiple utterances may be averaged to form a single word template. Furthermore, since most speech recognition systems do not require all of the speech information to be stored as a template, some type of data reduction is often performed by a training processor 170 to reduce the template memory requirements. The word templates are stored in template memory 160 for use by speech recognition processor 120 as well as by speech synthesis processor 140. The exact training procedure utilized by the preferred embodiment of the present invention may be found in the description accompanying FIG. 2.

In the recognition mode, speech recognition processor 120 compares the word feature information provided by acoustic processor 110 to the word recognition templates provided by template memory 160. If the acoustic features of the present word feature information derived from the user-spoken input speech sufficiently match the acoustic features of a particular prestored word template derived from the template memory, then recognition processor 120 provides device control data to device controller 130 indicative of the particular word recognized. A further discussion of an appropriate speech recognition apparatus, and how the preferred embodiment incorporates data reduction into the training process may be found in the description accompanying FIGS. 3 through 5.

Device controller 130 interfaces the entire control system to electronic device 150. Device controller 130 translates the device control data provided by recognition processor 120 into control signals adaptable for use by the particular electronic device. These control signals direct the device to perform specific operating functions as instructed by the user. (Device controller 130 may also perform additional supervisory functions related to other elements shown in FIG. 1.) An example of a device controller known in the art and suitable for use with the present invention is a microcomputer. Refer to FIG. 3 for further details of the hardware implementation.

Device controller 130 also provides device status data representing the operating status of electronic device 150. This data is applied to speech synthesis processor 140, along with word recogition templates from template memory 160. Synthesis processor 140 utilizes the status data to determine which word recognition template is to be synthesized into user-recognizable reply speech. Synthesis processor 140 may also include an internal reply memory, also controlled by the status data, to provide "canned" reply words to the user. In either case, the user is informed of the electronic device operating status when the speech reply signal is ouput via speaker 145.

Thus, FIG. 1 illustrates how the present invention provides a user-interactive control system utilizing speech recognition to control the operating parameters of an electronic device, and how a speech recognition template may be utilized to generate reply speech to the user indicative of the operating status of the device.

Figure 2:
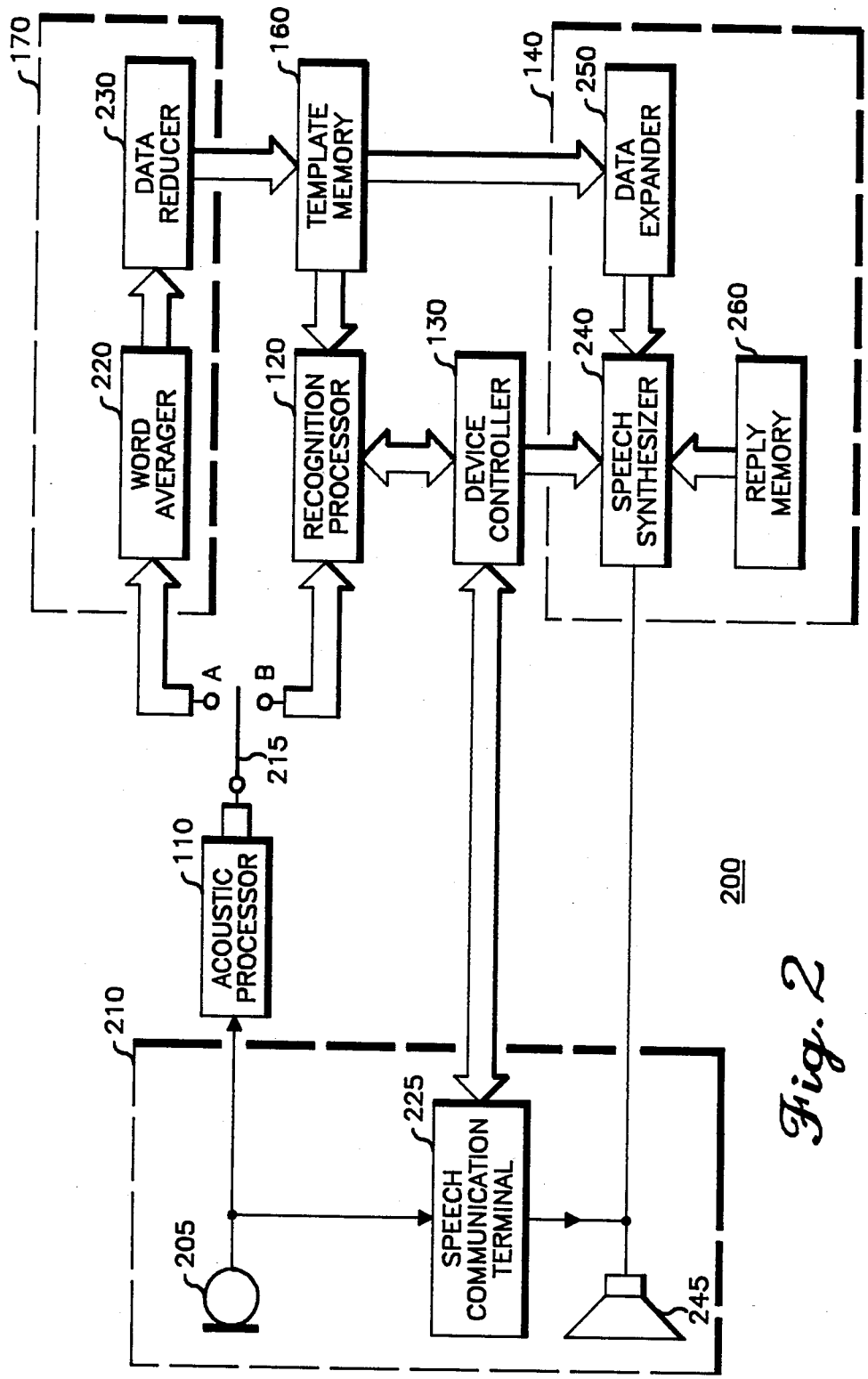
FIG. 2 is a block diagram of a speech communications device having a user-interactive control system employing speech recognition and speech synthesis in accordance with the present invention.

FIG. 2 illustrates in more detail the application of the user-interactive control system to a speech communications device comprising a part of any radio or landline voice communications system, such as, for example, a two-way radio system, a telephone system, an intercom system, etc. Acoustic processor 110, recognition processor 120, template memory 160, and device controller 130 are the same in structure and in operation as the corresponding blocks of FIG. 1. However, control system 200 illustrates the internal structure of speech communications device 210. Speech communication terminal 225 represents the main electronic network of device 210, such as, for example, a telephone terminal or a communications console. In this embodiment, microphone 205 and speaker 245 are incorporated into the speech communications device itself. A typical example of this microphone/speaker arrangement would be a telephone handset. Speech communications terminal 225 interfaces operating status information of the speech communications device to device controller 130. This operating status information may comprise functional status data of the terminal itself (e.g., channel data, service information, operating mode messages, etc.), user-feedback information of the speech recognition control system (e.g., directory contents, word recognition verification, operating mode status, etc.), or may include system status data pertaining to the communications link (e.g., loss-of-line, system busy, invalid access code, etc.).

In either the training mode or the recognition mode, the features of user spoken input speech are extracted by acoustic processor 110. In the training mode, which is represented in FIG. 2 by a position "A" of switch 215, the word feature information is applied to word averager 220 of training processor 170. As previously mentioned, if the system is designed to average multiple utterances together to form a single word template, the averaging is performed by word averager 220. Through the use of word averaging, the training processor can take into account the minor variances between two or more utterances of the same word, thereby producing a more reliable word template. Numerous word averaging techniques may be used. For example, one method would be to combine only the similar word features of all training utterances to produce a "best" set of features for the word template. Another technique may be to simply compare all training utterances to determine which one provides the "best" template. Still another word averaging technique is described by L. R. Rabiner and J. G. Wilson in "A Simplified Robust Training Procedure for Speaker Trained, Isolated Word Recognition Systems", *Journal of the Acoustic Society of America*, vol. 68 (November 1980), pp. 1271–76.

Data reducer 230 then performs data reduction upon either the averaged word data from word averager 220 or upon the word feature signals directly from acoustic processor 110, depending upon the presence or absence of a word averager. In either case, the reduction process consists of segmenting this "raw" word feature data and combining the data in each segment. The storage requirements for the template are then further reduced by differential encoding of the segmented data to produce "reduced" word feature data. This specific data reduction technique of the present invention is fully described in conjunction with FIGS. 4 and 5. To summarize, data reducer 230 compresses the raw word data to minimize the template storage requirements and to reduce the speech recognition computation time.

The reduced word feature data provided by training processor 170 is stored as word recognition templates in template memory 160. In the recognition mode, which is illustrated by position "B" of switch 215, recognition processor 120 compares the incoming word feature signals to the word recognition templates. Upon recognition of a valid command word, recognition processor 120 may instruct device controller 130 to cause a corresponding speech comunications device control function to be executed by speech communications terminal 225. Terminal 225 may respond to device controller 130 by sending operating status information back to controller 130 in the form of terminal status data. This data can be used by the control system to synthesize the appropriate speech reply signal to inform the user of the present device operating status. This sequence of events will be more clearly understood by referring to the subsequent example.

Synthesis processor 140 is comprised of speech synthesizer 240, data expander 250, and reply memory 260. A synthesis processor of this configuration is capable of generating "canned" replies to the user from a pre-stored vocabulary (stored in reply memory 260), as well as generating "template" responses from a user-generated vocabulary (stored in template memory 160). Speech synthesizer 240 and reply memory 260 are further described in conjunction with FIG. 3, and data expander 250 is fully described in the text accompanying FIG. 8a. In combination, the blocks of synthesis processor 140 generate a speech reply signal to speaker 245. Accordingly, FIG. 2 illustrates the technique of using a single template memory for both speech recognition and speech synthesis.

The simplified example of a "smart" telephone terminal employing voice-controlled dialing from a stored telephone number directory is now used to describe the operation of the control system of FIG. 2. Initially, an untrained speaker-dependent speech recognition system cannot recognize command words. Therefore, the user must manually prompy the device to begin the training procedure, perhaps by entering a particular code into the telephone keypad. Device controller 130 then directs switch 215 to enter the training mode (position "A"). Device controller 130 then instructs speech synthesizer 240 to respond with the predefined phrase TRAINING VOCABULARY ONE, which is a "canned" response obtained from reply memory 260. The user then begins to build a command word vocabulary by uttering command words, such as STORE or RECALL, into microphone 205. The features of the utterance are first extracted by acoustic processor 110, and then applied to either word averager 220 or data reducer 230. If the particular speech recognition system is designed to accept multiple utterances of the same word, word averager 220 produces a set of averaged word features representing the best representation of that particular word. If the system does not have word averaging capabilities, the single utterance word features (rather than the multiple utterance averaged word features) are applied to data reducer 230. The data reduction process removes unnecessary or duplicate feature data, compresses the remaining data, and provides template memory 160 with "reduced" word recognition templates. A similar procedure is followed for training the system to recognize digits.

Once the system is trained with the command word vocabulary, the user must continue the training procedure by entering telephone directory names and numbers. To accomplish this task, the user utters the previously-trained command word ENTER. Upon recognition of this utterance as a valid user command, device controller 130 instructs speech synthesizer 240 to reply with the "canned" phrase DIGITS PLEASE? stored in reply memory 260. Upon entering the appropriate telephone number digits (e.g., 555-1234), the user says TERMINATE and the system replys NAME PLEASE? to prompt user-entry of the corresponding directory name (e.g., SMITH). This user-interactive process continues until the telephone number directory is completely filled with the appropriate telephone names and digits.

To place a phone call, the user simply utters the command word RECALL. When the utterance is recognized as a valid user command by recognition processor 120, device controller 130 directs speech synthesizer 240 to generate the verbal reply NAME? via synthesizing information provided by reply memory 260. The user then responds by speaking the name in the directory index corresponding to the telephone number that he desires to dial (e.g. JONES). The word will be recognized as a valid directory entry if it corresponds to a predetermined name index stored in template memory 160. If valid, device controller 130 directs data expander 250 to obtain the appropriate reduced word recognition template from template memory 160 and perform the data expansion process for synthesis. Data expander 250 "unpacks" the reduced word feature data and restores the proper energy contour for an intelligible reply word. The expanded word template data is then fed to speech synthesizer 240. Using both the template data and the reply memory data, speech synthesizer 240 generates the phrase JONES . . . (from template memory 160 through data expander 250) . . . FIVE-FIVE-FIVE, SIX-SEVEN-EIGHT-NINE (from reply memory 260).

The user then says the command word SEND which, when recognized by the control system, instructs device controller 130 to send telephone number dialing information to speech communications terminal 225. Terminal 225 outputs this dialing information via a appropriate communications link. When the telephone connection is made, speech communications terminal 225 interfaces microphone audio from microphone 205 to the appropriate transmit path, and receive audio from the appropriate receive audio path to speaker 245. If a proper telephone connection cannot be made, terminal controller 225 provides the appropriate communications link status information to device controller 130. Accordingly, device controller 130 instructs speech synthesizer 240 to generate the appropriate reply word corresponding to the status information provided, such as the reply word SYSTEM BUSY. In this manner, the user is informed of the communications link status, and user-interactive voice-controlled directory dialing is achieved.

The above operational description is merely one application of synthesizing speech from speech recognition templates according to the present invention. Numerous other applications of this novel technique to a speech communications device are contemplated, such as, for example, a communications console, a two-way radio, etc. In the preferred embodiment, the control system of the present invention is used with a mobile radiotelephone.

Although speech recognition and speech synthesis allows a vehicle operator to keep both eyes on the road, the conventional handset or hand-held microphone prohibits him from keeping both hands on the steering wheel or from executing proper manual (or automatic) transmission shifting. For this reason, the control system of the preferred embodiment incorporates a speakerphone to provide hands-free control of the speech communications device. The speakerphone performs the transmit/receive audio switching function, as well as the received/reply audio multiplexing function.

Referring now to FIG. 3, control system 300 utilizes the same acoustic processor block 110, training processor block 170, recognition processor block 120, template memory block 160, device controller block 130, and synthesis processor block 140 as the corresponding blocks of FIG. 2. However, microphone 302 and speaker 375 are not an integral part of the speech communications terminal. Instead, input speech signal from microphone 302 is directed to radiotelephone 350 via speakerphone 360. Similarly, speakerphone 360 also controls the mulitplexing of the synthesized audio from the control system and the receive audio from the communications link. A more detailed analysis of the switching/multiplexing configuration of the speakerphone will be described later. Additionally, the speech communications terminal is now illustrated in FIG. 3 as a radiotelephone having a transmitter and a receiver to provide the appropriate communications link via radio frequency (RF) channels. A detailed description of the radio blocks is also provided later.

Microphone 302, which is typically remotely-mounted at a distance from the user's mouth (e.g., on the automobile sun visor), acoustically couples the user's voice to control system 300. This speech signal is usually amplified by preamplifier 304 to provide input speech signal 305. This audio input is directly applied to acoustic processor 110, and is switched by speakerphone 360 before being applied to radiotelephone 350 via switched microphone audio line 315.

As previously mentioned, acoustic processor 110 extracts the features of the user-spoken input speech to provide word feature information to both training processor 170 and recognition processor 120. Acoustic processor 110 first converts the analog input speech into digital form by analog-to-digital (A/D) converter 310. This digital data is then applied to feature extractor 312, which digitally performs the feature extraction function. Any feature extraction implementation may be utilized in block 312, but the present embodiment utilizes a particular form of "channel bank" feature extraction. Under the channel bank approach, the audio input signal frequency spectrum is divided into individual spectral bands by a bank of bandpass filters, and the appropriate word feature data is generated according to an estimate of the amount of energy present in each band. A feature extrator of this type is described in the article: "The Effects of Selected Signal Processing Techniques on the Performance of a Filter Bank Based Isolated Word Recognizer", B. A. Dautrich, L. R. Rabiner, and T. B. Martin, *Bell System Technical Journal*, vol. 62, no. 5, (May-June 1983), pp. 1311-1335. An appropriate digital filter algorithm is described in Chapter 4 of the L. R. Rabiner and B. Gold, *Theory and Application of Digital Signal Processing*, (Prentice Hall, Englewood Cliffs, N.J., 1975).

Training processor 170 utilizes this word feature data to generate word recognition templates to be stored in template memory 160. First of all, endpoint detector 318 locates the appropriate beginning and end locations of the user's words. These endpoints are based upon the time-varying overrall energy estimate of the input word feature data. An endpoint detector of this type is described by L. R. Rabiner and M. R. Sambur in "An Algorithm for Determining the Endpoints of Isolated Utterances," *Bell System Technical Journal,* vol. 54, no. 2, (February 1975), pp. 297–315.

Word averager 320 then combines the several utterances of the same word spoken by the user to provide a more reliable template. As previously described in FIG. 2, any appropriate word averaging scheme may be utilized, or the word averaging function may be entirely omitted.

Data reducer 322 utilizes the "raw" word feature data from word averager 320 to generate "reduced" word feature data for storage in template memory 160 as reduced word recognition templates. The data reduction process basically consists of normalizing the energy data, segmenting the word feature data, and combining the data in each segment. After the combined segments have been generated, the storage requirements are further reduced by differential encoding of the filter data. The actual normalization, segmentation, and differential encoding steps of data reducer 322 are described in detail in conjunction with FIGS. 4 and 5. For a general memory map illustrating the reduced data format of template memory 160, refer to FIG. 6c.

Endpoint detector 318, word averager 320, and data reducer 322 comprise training processor 170. In the training mode, training control signal 325, from device controller 130, instructs these three blocks to generate new word templates for storage in template memory 160. However, in the recognition mode, training control signal 325 directs these blocks to suspend the process of generating new word templates, since this function is not desired during speech recognition. Hence, training processor 170 is only used in the training mode.

Template memory 160 stores word recognition templates to be matched to the incoming speech in recognition processor 120. Template memory 160 is typically comprised of a standard Random Access Memory (RAM), which may be organized in any desired address configuration. A general purpose RAM which may be used with a speech recognition system is the Toshiba 5565 8k×8 static RAM. However, a non-volatile RAM is preferred such that word templates are retained when the system is turned off. In the present embodiment, an EEPROM (Electrically-erasable, programmable read-only memory) functions as template memory 160.

Word recognition templates, stored in template memory 160, are provided to speech recognition processor 120 and speech synthesis processor 140. In the recognition mode, recognition processor 120 compares these previously stored word templates against the input word features provided by acoustic processor 110. In the present embodiment, recognition processor 120 may be thought of as being comprised of two distinct blocks—template decoder 328 and speech recognizer 326. Template decoder 328 interprets the reduced feature data provided by the template memory, such that speech recognizer 326 can perform its comparison function. Briefly described, template decoder 328 implements an efficient "nibble-mode access technique" of obtaining the reduced data from template storage, and performs differential decoding on the reduced data such that speech recognizer 326 can utilize the information. Template decoder 328 is described in detail in the text accompanying FIG. 7b.

Hence, the technique is implementing data reducer 322 to compress the feature date into a reduced data format for storage in template memory 160, and the use of template decoder 328 to decode the reduced word template information, allows the present invention to minimize template storage requirements.

Figure 7A:
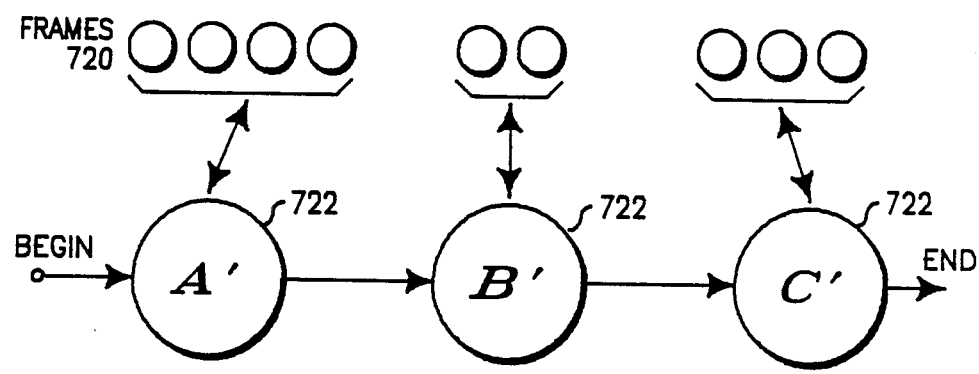
FIG. 7a is a graphical representation of frames clustered into average frames, each average frame represented by a state in a word model, in accordance with the present invention.

Speech recognizer 326, which performs the actual speech recognition comparison process, may use one of several speech recognition algorithms. The recognition algorithm of the present embodiment incorporates near-continuous speech recognition, dynamic time warping, energy normalization, and a Chebyshev distance metric to determine a template match. Refer to FIG. 7a et seq. for a detailed description. Prior art recognition algorithms, such as described in J. S. Bridle, M. D. Brown, and R. M. Chamberlain, "An Algorithm for Connected Word Recognition," *IEEE International Conference on Acoustics, Speech, and Signal Processing,* May 3–5 1982, vol. 2, pp. 899–902, may also be used.

In the present embodiment, an 8-bit microcomputer performs the function of speech recognizer 326. Moreover, several other control system blocks of FIG. 3 are implememted in part by the same microcomputer with the aid of a CODEC/FILTER and a DSP (Digital Signal Processor). An alternate hardware configuration for speech recognizer 326, which may be used in the present invention is described in an article by J. Peckham, J. Green, J. Canning, and P. Stevens, entitled "A Real-Time Hardware Continuous Speech Recognition System," *IEEE International Conference on Acoustics, Speech, and Signal Processing,* (May 3–5 1982), vol. 2, pp. 863–866, and the references contained therein. Hence, the present invention is not limited to any specific hardware or any specific type of speech recognition. More particularly, the present invention contemplates the use of: isolated or continuous word recognition; and a software-based or hardware-based implementation.

Device controller 130, consisting of control unit 334 and directory memory 332, serves to interface speech recognition processor 120 and speech synthesis processor 140 to radiotelephone 350 via two-way interface busses. Control unit 334 is typically a controlling microprocessor which is capable of interfacing data from radio logic 352 to the other blocks of the control system. Control unit 334 also performs operational control of radiotelephone 350, such as: unlocking the control head; placing a telephone call; ending a telephone call; etc. Depending on the particular hardware interface structure to the radio, control unit 334 may incorporate other sub-blocks to perform specific control functions as DTMF dialing, interface bus multiplexing, and control-function decision-making. Moreover, the data-interfacing function of control unit 334 can be incorporated into the existing hardware of radio logic 352. Hence, a hardware-specific control program would typically be provided for each type of radio or for each kind of electronic device application.

Directory memory 332, an EEPROM, stores the plurality of telephone numbers, thereby permitting directory dialing. Stored telephone number directory information is sent from control unit 334 to directory memory 332 during the training process of entering telephone numbers, while this directory information is provided to control unit 334 in response to the recognition of a valid directory dialing command. Depending on the particular device used, it may be more economical to incorporate directory memory 332 into the telephone device itself. In general, however, controller block 130 performs the telephone directory storage function, the telephone number dialing function, and the radio operational control function.

Controller block 130 also provides different types of status information, representing the operating status of the radiotelephone, to speech synthesis processor 140. This status information may include information as to the telephone numbers stored in directory memory 332 ("555-1234", etc.), directory names stored in template memory 160 ("Smith", "Jones", etc.), directory status information ("Directory Full", "Name?", etc.), speech recognition status information ("Ready", "User Number?", etc.), or radiotelephone status information ("Call Dropped", "System Busy", etc.). Hence, controller block 130 is the heart of the user-interactive speech recognition/speech synthesis control system.

Figure 8A:
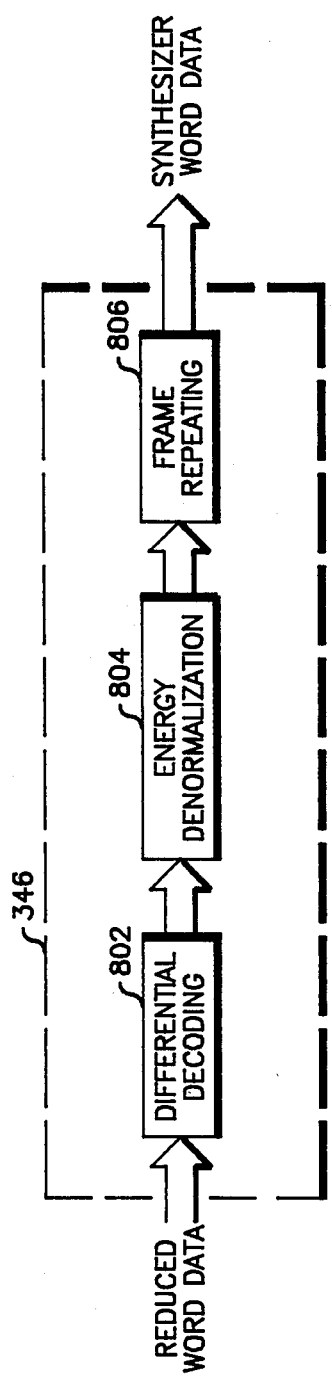
FIG. 8a is a detailed block diagram of the data expander block 346 of FIG. 3.

Speech synthesis processor block 140 performs the voice reply function. Word recognition templates, stored in template memory 160, are provided to data expander 346 whenever speech synthesis from a template is required. As previously mentioned, data expander 346 "unpacks" the reduced word feature data from template memory 160 and provides "template" voice response data for channel bank speech synthesizer 340. Refer to FIG. 8a et seq. for a detailed explanation of data expander 346.

If the system controller determines that a "canned" reply word is desired, reply memory 344 supplies voice reply data to channel bank speech synthesizer 340. Reply memory 344 typically comprises a ROM or an EPROM. In the preferred embodiment, an Intel TD27256 EPROM is used as reply memory 344.

Using either the "canned" or "template" voice reply data, channel bank speech synthesizer 340 synthesizes these reply words, and outputs them to digital-to-analog (D/A) converter 342. The voice reply is then routed to the user. In the present embodiment, channel bank speech synthesizer 340 is the speech synthesis portion of a 14-channel vocoder. An example of such a vocoder may be found in J. N. Holmes, "The JSRU Channel Vocoder", *IEEE PROC.*, vol. 127, pt. F, no. 1, (February, 1980), pp. 53-60. The information provided to a channel bank synthesizer normally includes whether the input speech should be voiced or unvoiced, the pitch rate if any, and the gain of each of the 14 filters. However, as will be obvious to those skilled in the art, any type of speech synthesizer may be utilized to perform the basic speech synthesis function. The particular configuration of channel bank speech synthesizer 340 is fully described in conjunction with FIG. 9a et seq.

As we have seen, the present invention teaches the implementation of speech synthesis from a speech recognition template to provide a user-interactive control system for a speech communications device. In the present embodiment, the speech communications device is a radio transceiver, such as a cellular mobile radiotelephone. However, any speech communications device warranting hands-free user-interactive operation may be used. For example, any simplex radio transceiver requiring hands-free control may also take advantage of the improved control system of the present invention.

Referring now to radiotelephone block 350 of FIG. 3, radio logic 352 performs the actual radio operational control function. Specifically, it directs frequency synthesizer 356 to provide channel information to transmitter 353 and receiver 357. The function of frequency synthesizer 356 may also be performed by crystal-controlled channel oscillators. Duplexer 354 interfaces transmitter 353 and receiver 357 to a radio frequency (RF) channel via antenna 359. in the case of a simplex radio transceiver, the function of duplexer 354 may be performed by an RF switch. For a more detailed explanation of representative radiotelephone circuitry, refer to Motorola Instruction Manual 68P81066E40 entitled "DYNA T.A.C. Cellular Mobile Telephone."

Speakerphone 360, also termed a VSP (vehicular speakerphone) in the present application, provides hands-free acoustic coupling of: the user-spoken audio to the cotrol system and to the radio telephone transmitter audio; the synthesized speech reply signal to the user; and the received audio from the radiotelephone to the user. As previously noted, preamplifier 304 may perform amplification upon the audio signal provided by microphone 302 to produce input speech signal 305 to acoustic processor 110. This input speech signal is also applied to VSP transmit audio switch 362, which routes input signal 305 to radio transmitter 353 via transmit audio 315. VSP transmit switch 362 is controlled by VSP signal detector 364. Signal detector 364 compares input signal 305 amplitude against that of receive audio 355 to perform the VSP switching function.

When the mobile radio user is talking, signal detector 364 provides a positive control signal via detector output 361 to close transmit audio switch 362, and a negative control signal via detector output 363 to open receive audio switch 368. Conversely, when the landline party is talking, signal detector 364 provides the opposite polarity signals to close receive audio switch 368, while opening transmit audio switch 362. When the receive audio switch is closed, receiver audio 355 from radiotelephone receiver 357 is routed through receive audio switch 368 to multiplexer 370 via switched receive audio output 367. In some communications systems, it may prove advantageous to replace audio switches 362 and 368 with variable gain devices that provide equal but opposite attenuations in response to the control signals from the signal detector. Multiplexer 370 switches between voice reply audio 345 and switched receive audio 367 in response to multiplex signal 335 from control unit 334. Whenever the control unit sends status information to the speech synthesizer, multiplexer signal 335 directs multiplexer 370 to route the voice reply audio to the speaker. VSP audio 365 is usually amplified by audio amplifier 372 before being applied to speaker 375. It is to be noted that the vehicle speakerphone embodiment described herein is only one of numerous possible configurations which can be used in the present invention.

In summary, FIG. 3 illustrates a radiotelephone having a hands-free user-interactive speech-recognizing control system for controlling radiotelephone operating parameters upon a user-spoken command. The control system provides audible feedback to the user via speech synthesis from speech recognition template memory or a "canned" response reply memory. The vehicle speakerphone provides hands-free acoustic coupling of the user-spoken input speech to the control system and to the radio transmitter, the speech reply signal from the control system to the user, and the receiver audio to the user. The implementation of speech synthesis from recognition templates significantly improves the performance and versatility of the radiotelephone's speech recognition control system.

2. Data Reduction and Template Storage

Figure 4A:
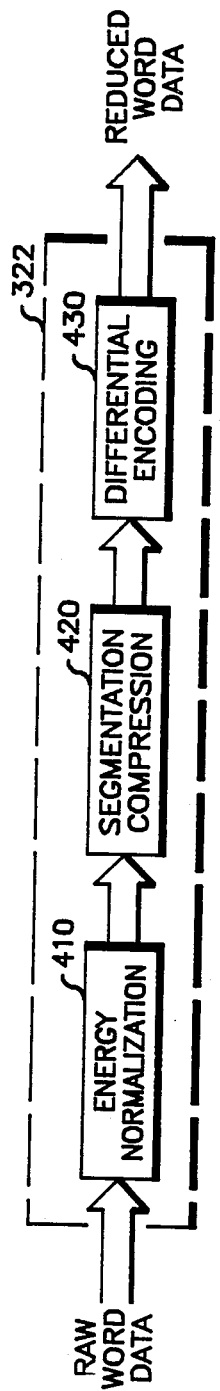
FIG. 4a is an expanded block diagram of the data reducer block 322 of FIG. 3.

Referring to FIG. 4a, an expanded block diagram of data reducer 322 is shown. As previously stated, data reducer block 322 utilizes raw word feature data from word averager 320 to generate reduced word feature data for storage in template memory 160. The data reduction function is performed in three steps: (1) energy normalization block 410 reduces the range of stored values for channel energies by subtracting the average value of the channel energies; (2) segmentation/compression block 420 segments the word feature data and combines acoustically similar frames to form "clusters"; and (3) differential encoding block 430 generates the differences between adjacent channels for storage, rather than the actual channel energy data, to further reduce storage requirements. When all three processes have been performed, the reduced data format for each frame is stored in only nine bytes as shown in FIG. 6c. In short, data reducer 322 "packs" the raw word data into a reduced data format to minimize storage requirements.

Figure 4B:
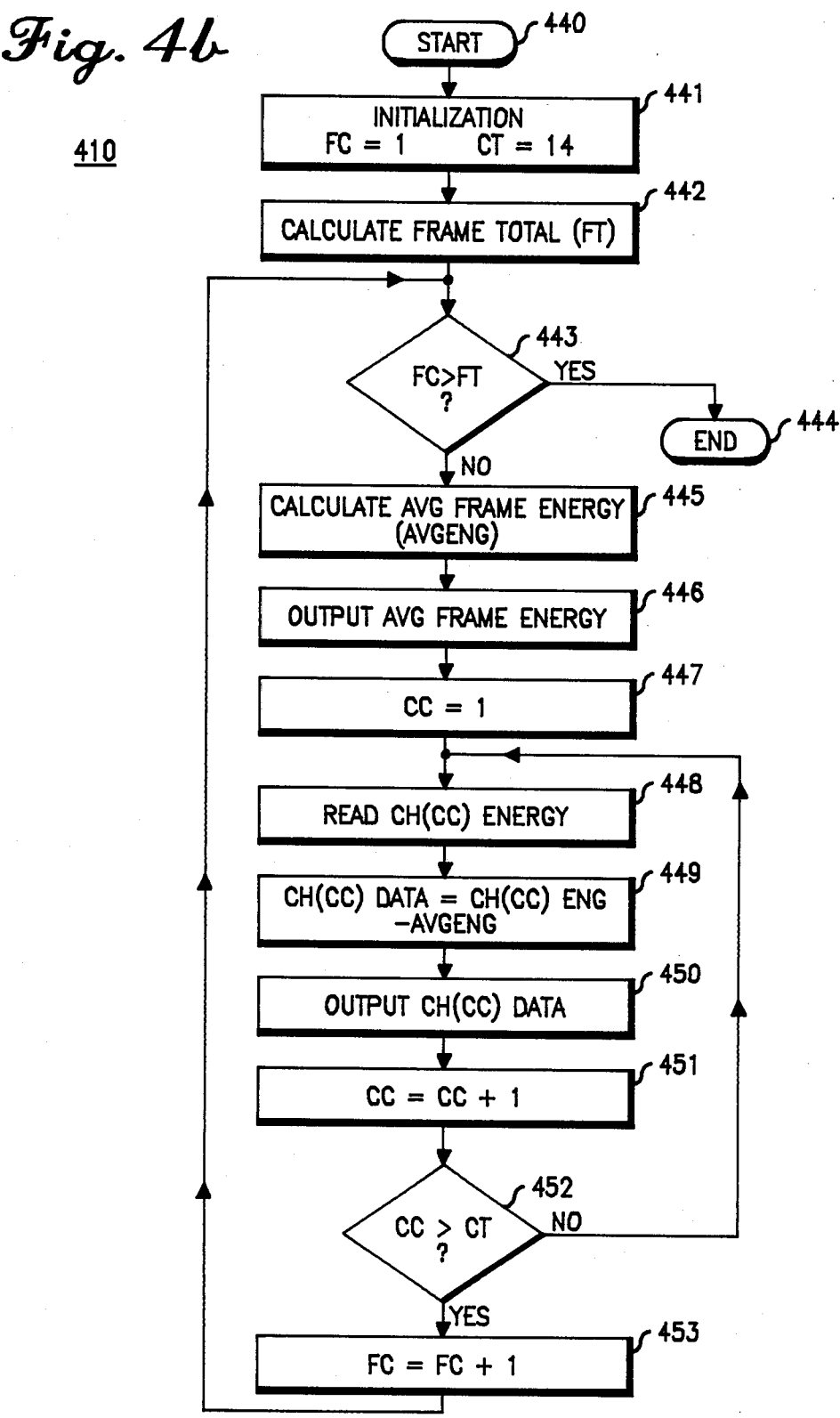

The flowchart of FIG. 4b illustrates the sequence of steps performed by energy normalization block 410 of the previous Figure. Upon starting at block 440, block 441 initializes the variables which will be used in later calculations. Frame count FC is initialized to one to correspond to the first frame of the word to be data reduced. Channel total CT is initialized to the total number of channels corresponding to those of the channel bank feature extractor 312. In the preferred embodiment, a 14-channel feature extractor is used.

Next, the frame total FT is calculated in block 442. Frame total FT is the total number of frames per word to be stored in the template memory. This frame total information is available from training processor 170. To illustrate, say that the acoustic features of a 500 millisecond duration input word are (digitally) sampled every 10 milliseconds. Each 10 millisecond time segment is called a frame. The 500 millisecond word then comprises 50 frames. Thus, FT would equal 50.

Block 443 tests to see if all the frames of the word have been processed. If the present frame count FC is greater than the frame total FT, no frames of the word would be left to normalize, so the energy normalization process for that word will end at block 444. If, however, FC is not greater than FT, the energy normalization process continues with the next frame of the word. Continuing with the above example of a 50-frame word, each frame of the word is energy normalized in blocks 445 through 452, the frame count FC is incremented in block 453, and FC is tested in block 443. After the 50th frame of the word has been energy normalized, FC will be incremented to 51 in block 435. When a frame count FC of 51 is compared to the frame total FT of 50, block 443 is terminate the energy normalization process at block 444.

The actual energy normalization procedure is accomplished by subtracting the average value of all of the channels from each individual channel to reduce the range of values stored in the template memory. In block 445, the average frame energy (AVGENG) is calculated according to the formula:

$$AVGENG = \sum_{i=1}^{i=CT} CH(i)/CT.$$

where CH(i) is the individual channel energies, and where CT equals the total number of channels. It should be noted that in the present embodiment, energies are stored as log energies and the energy normalization process actually subtracts the average log energy from the log energy of each channel.

The average frame energy AVGENG is output in block 446 to be stored at the end location of the channel data for each frame. (See FIG. 6c byte 9.) In order to efficiently store the average frame energy in four bits, AVGENG is normalized to the peak energy value of the entire template, and then quantized to 3 dB steps. When the peak energy is assigned a value of 15 (the four-bit maximum), the total energy variation within a template would be 16 steps×3 dB/step=48 dB. In the preferred embodiment, this average energy normalization/quantization is performed after the differential encoding of channel 14 (FIG. 6a) to permit higher precision calculations during the segmentation/compression process (block 420).

Block 447 sets the channel count CC to one. Block 448 reads the channel energy addressed by the channel counter CC into an accumulator. Block 449 subtracts the average energy calculated in block 445 from the channel energy read in block 448. This step generates normalized channel energy data, which is then output (to segmentation/compression block 420) in block 450. Block 451 increments the channel counter, and block 452 tests to see if all channels have been normalized. If the new channel count is not greater than the channel total, then the process returns to block 448 where the next channel energy is read. If, however, all channels of the frame have been normalized, the frame count is incremented in block 453 to obtain the next frame of data. When all frames have been normalized, the energy normalization process of data reducer 322 ends at block 444.

Refering now to FIG. 4c, shown is a block diagram illustrating an implementation of the data reducer, block 420. The input feature data is stored in frames in initial frame storage, block 502. The memory used for storage is preferred to be RAM. A segmentation controller, block 504, is used to control and to designate which frames will be considered for clustering. A number of microprocessors can be used for this purpose, such as the Motorola type 6805 microprocessor.

The present invention requires that incoming frames be considered for averaging by first calculating a distortion measure associated with the frames to determine the similarity between the frames before averaging. The calculation is preferably made by a microprocessor, similar to, or the same as that used in block 504. Details of the calculation are subsequently discussed.

Once it has been determined which frames will be combined, the frame averager, block 508, combines the frames into a representative average frame. Again, similar type processing means, as in block 504, can be used for combining the specified frames for averaging.

To effectively reduce the data, the resulting word templates should occupy as little template storage as possible without being distorted to the point that the recognition process is degraded. In other words, the amount of information representing the word templates should be minimized, while, at the same time, maximizing the recognition accuracy. Although the two extremes are contradictory, the word template data can be minimized if a minimal level of distortion is allowed for each cluster.

FIG. 5a illustrates a method for clustering frames for a given level of distortion. Speech is depicted as feature data grouped in frames 510. The five center frames 510 form a cluster 512. The cluster 512 is combined into a representative average frame 514. The average frame 514 can be generated by any number of well averaging methods according to the particular type of feature data used in the system. To determine whether a cluster meets the allowable distortion level, a prior art distortion test can be used. However, it is preferred that the average frame 514 be compared to each of the frames 510 in the cluster 512 for a measure of similarity. The distance between the average frame 514 and each frame 510 in the cluster 512 is indicated by distances D1-D5. If one of these distances exceeds the allowable distortion level, the threshold distance, the cluster 512 is not considered for the resulting word template. If the threshold distance is not exceeded, the cluster 512 is considered as a possible cluster represented as the average frame 514.

This technique for determining a valid cluster is referred to as a peak distortion measure. The present embodiment uses 2 types of peak distortion criteria, peak energy distortion and peak spectural distortion. Mathematically, this is stated as follows:

$D = \max[D1, D2, D3, D4, D5]$, where D1-D5, as discussed above, represent each distance.

These distortion measures are used as local constraints for restricting which frames may be combined into an average frame. If D exceeds a predetermined distortion threshold for either energy or spectral distortion, the cluster is rejected. By maintaining the same constraints for all clusters, a relative quality of the resulting word template is realized.

This clustering technique is used with dynamic programming to optimally reduce the data representing the word template. The principle of dynamic programming can be mathematically stated as follows:

$Y_o = 0$ and
$Y_j = \min[Y_i + C_{ij}]$, for all i, where $Y_j$ is the cost of the least cost path from node 0 to node j and $C_{ij}$ is the cost incurred in moving from node i to node j. The integer values of i and j range over the possible number of nodes.

To apply this principle to the reduction of word templates in accordance with the present invention, several assumptions are made. They are:

The information in the templates is in the form of a series of frames, spaced equally in time;
A suitable method of combining frames into an average frame exists;
A meaningful distortion measure exists for comparing an average frame to an original frame; and
Frames may be combined only with adjacent frames.

The end objective of the present invention is to find the minimal set of clusters representing the template, subject to the constraint that no cluster exceeds a predetermined distortion threshold.

The following definitions allow the principle of dynamic programming to be applied to data reduction according to the present invention.

$Y_j$ is the combination of clusters for the first j frames;
$Y_o$ is the null path, meaning there are no clusters at this point;
$C_{ij} = 1$ if the cluster of frames, i+1 through j, meets the distortion critera, $C_{ij}$ = infinity otherwise.

The clustering method generates optimal cluster paths starting at the first frame of the word template. The cluster paths assigned at each frame within the template are referred to as partial paths since they do not completely define the clustering for the entire word. The method begins by initializing the null path, associated with 'frame 0', to 0, i.e. $Y_o = 0$. This indicates that a template with zero frames has zero clusters associated with it. A total path distortion is assigned to each path to describe its relative quality. Although any total distortion measure can be used, the implementation described herein uses the maximum of the peak spectral distortions from all the clusters defining the current path. Accordingly, the null path, $Y_o$, is assigned zero total path distortion, TPD.

To find the first partial path or combination of clusters, partial path Y1 is defined as follows:

Y1 (partial path at frame one) = Y0+C0,1

This states that the allowable clusters of one frame can be formed by taking the null path, Y0, and appending all frames up to frame 1. Hence, the total cost for partial path Y1 is 1 cluster and the total path distortion is zero, since the average frame is identical to the actual frame.

The formation of the second partial path, Y2, requires that two possibilities be considered. They are:
Y2 = min [Y0+C0,2;
Y1+C1,2].

The first possibility is the null path, Y0, with frames 1 and 2 combined into one cluster. The second possibility is the first frame as a cluster, partial path Y1, plus the second frame as the second cluster.

The first possibility has a cost of one cluster while the second has a cost of two clusters. Since the object in optimizing the reduction is to obtain the fewest clusters, the first possibility is preferred. The total cost for the first possibility is one cluster. Its TPD is equal to the peak distortion between each frame and the average of the two frames. In the instance that the first possibility has a local distortion which exceeds the predetermined threshold, the second possibility is chosen.

To form partial path Y3, three possibilities exist:
Y3 = min [Y0+C0,3;
Y1+C1,3;
Y2+C2,3].

The formation of partial path Y3 depends upon which path was chosen during the formation of partial path Y2. One of the first two possibilities is not considered, since partial path Y2 was optimally formed. Hence, the path that was not chosen at partial path Y2 need not be considered for partial path Y3. In carrying out this technique for large numbers of frames, a globally optimal solution is realized without searching paths that will never become optimum. Accordingly, the computation time required for data reduction is substantially reduced.

FIG. 5b illustrates an example of forming the optimal partial path in a four frame word template. Each partial path, Y1 through Y4, is shown in a separate row. The frames to be considered for clustering are underlined. The first partial path, defined as Y0+C0,1, has only one choice, 520. The single frame is clustered by itself.

For partial path Y2, the optimal formation includes a cluster with the first two frames, choice 522. In this example, assume the local distortion threshold is exceeded, therefore the second choice 524 is taken. The X over these two combined frames 522 indicates that combining these two frames will no longer be held as a consideration for a viable average frame. Hereinafter, this is referred to as an invalidated choice. The optimal cluster formation up to frame 2 comprises two clusters, each with one frame 524.

For partial path Y3, there are three sets of choices. The first choice 526 is the most desirable but it would typically be rejected since combining the first two frames 522 of partial path Y2 exceeds the threshold. It should be noted that this is not always the case. A truly optimal algorithm would not immediately reject this combination based solely on the invalidated choice 522 of partial path Y2. The inclusion of additional frames into a cluster which already exceeds the distortion threshold occasionally causes the local distortion to decrease. However, this is rare. In this example, such an inclusion is not considered. Larger combinations of an invalidated combination will also be invalidated. Choice 530 is invalidated because choice 522 was rejected. Accordingly, an X is depicted over the first and third choices 526 and 530, indicating an invalidation of each. Hence, the third partial path, Y3, has only two choices, the second 528 and the fourth 532. The second choice 528 is more optimal (fewer clusters) and, in this example, is found not to exceed the local distortion threshold. Accordingly, the fourth choice 532 is invalidated since it is not optimal. This invalidation is indicated by the XX over the fourth choice 532. The optimal cluster formation up to frame 3 comprises two clusters 528. The first cluster contains only the first frame. The second cluster contains frames 2 and 3.

The fourth partial path, Y4, has four conceptual sets from which to choose. The X indicates that choices 534, 538, 542 and 548 are invalidated as a consequence of choice 522, from the second partial path, Y2, being invalidated. This results in consideration of only choices 536, 540, 544 and 546. Since choice 546 is known to be a non-optimal choice, since the optimal clustering up to Y3 is 528 not 532, it is invalidated, as indicated by XX. Choice 536, of the remaining three choices, is selected next, since it minimizes the number of representative clusters. In this example, choice 536 is found not to exceed the local distortion threshold. Therefore, the optimal cluster formation for the entire word template comprises only two clusters. The first cluster contains only the first frame. The second cluster contains frames 2 through 4. Partial path Y4 represents the optimally reduced word template. Mathematically, this optimal partial path is defined as: Y1+C1,4.

The above path forming procedure can be improved upon by selectively ordering the cluster formations for each partial path. The frames can be clustered from the last frame of the partial path toward the first frame of the partial path. For example, in forming a partial path Y10, the order of clustering is: Y9+C0,10; Y8+C8,10; Y7+C7,10; etc. The cluster consisting of frame 10 is considered first. Information defining this cluster is saved and frame 9 is added to the cluster, C8,10. If clustering frames 9 and 10 exceeds the local distortion threshold, then the information defining cluster C9,10 is not considered an additional cluster appended to partial path Y9. If clustering frames 9 and 10 does not exceed the local distortion threshold, then cluster C8,10 is considered. Frames are added to the cluster until the threshold is exceeded, at which time the search for partial paths at Y10 is completed. Then, the optimal partial path, path with least clusters, is chosen from all the preceding partial paths for Y10. This selective order of clustering limits the testing of potential cluster combinations, thereby reducing computation time.

Figure 5C:
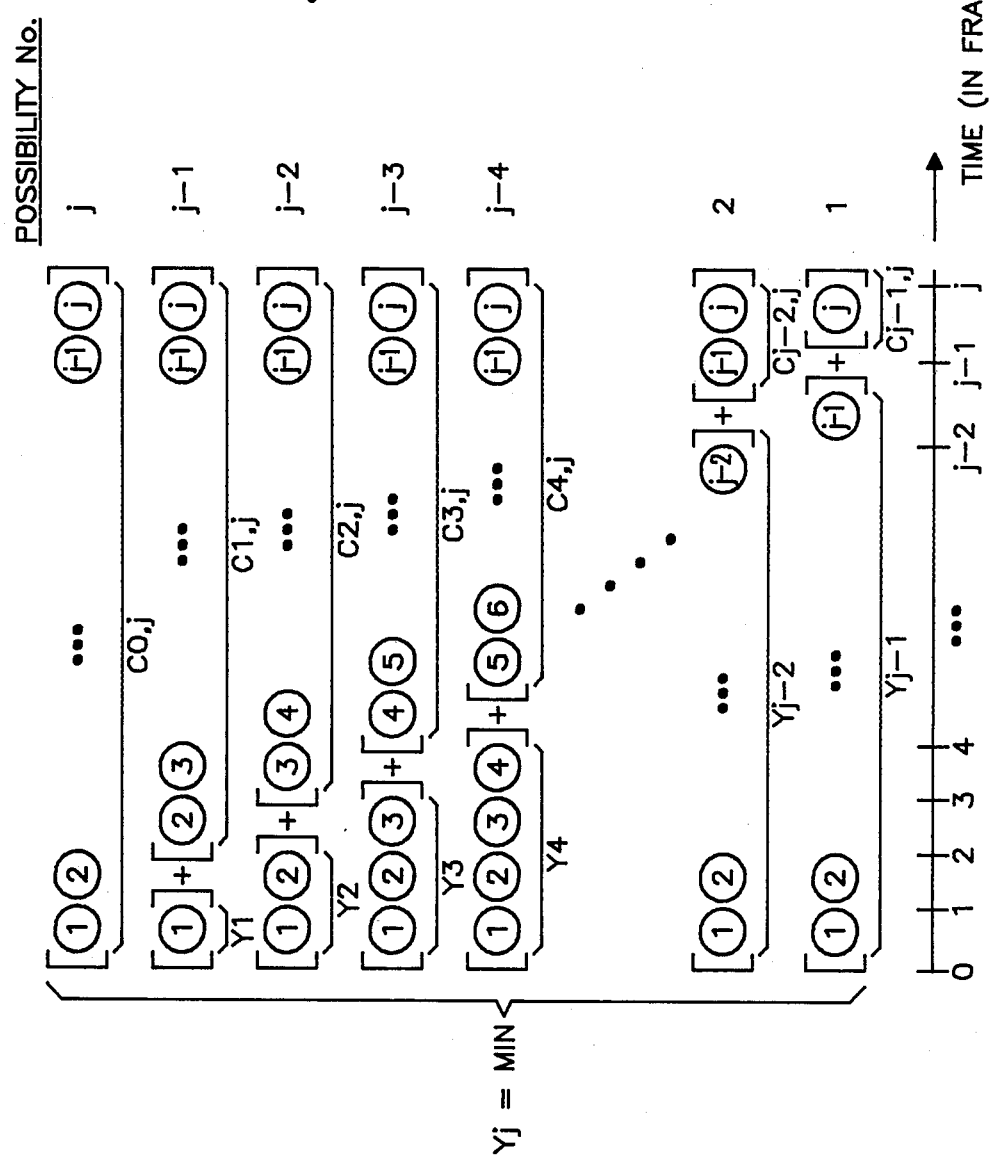
FIG. 5c is a table showing the possible formations of an arbitrary partial cluster path according to the present invention.

In general, at an arbitrary partial path Yj, a maximum of j cluster combinations are tested. FIG. 5c illustrates the selective ordering for such a path. The optimal partial path is mathematically defined as:

$$Y_j = \min[Y_{j-1} + C_{j-1,J}; \ldots ; Y_1 + C_{1,j}; Y_0 + C_{0,j}].$$

where min is min number of clusters in cluster path that satisfies distortion criteria. Marks are placed on the horizontal axis of FIG. 5c, depicting each frame. The rows shown vertically are cluster formation possibilities for partial path Yj. The lowest set of brackets, cluster possibility number 1, determines the first potential cluster formation. This formation includes the single frame, j, clustered by itself and the optimal partial path Yj−1. To determine if a path exists with a lower cost, possibility two is tested. Since partial path Yj−2 is optimal up to frame j−2, clustering frames j and j−1 determines if another formation exists up to frame j. Frame j is clustered with additional adjacent frames until the distortion threshold is exceeded. When the distortion threshold is exceeded, the search for partial path Yj is completed and the path with the fewest clusters is taken as Yj.

Ordering the clustering in this manner forces only frames immediately adjacent to frame j to be clustered. An additional benefit is that invalidated choices, are not used in determining which frames should be clustered. Hence, for any single partial path, a minimum number of frames are tested for clustering and only information defining one clustering per partial path is stored in memory.

The information defining each partial path includes three parameters:
(1) The total path cost, i.e., the number of clusters in the path.
(2) A trace-back pointer indicating the previous path formed. For example, if partial path Y6 is defined as (Y3+C3,6), then the trace-back pointer for Y6 points to partial path Y3.
(3) The total path distortion (TPD) for the current path, reflecting the overall distortion of the path.

The traceback pointers define the clusters within the path.

The total path distortion reflects the quality of the path. It is used to determine which of two possible path formations, each having equal minimal cost (number of clusters), is the most desirable.

The following example illustrates an application of these parameters.

Let the following combinations exist for partial path Y8:

$$Y8 = Y3 + C_{3,8} \text{ or } Y5 + C_{5,8}.$$

Let the cost of partial path Y3 and partial path Y5 be equal and let clusters C3,8 and C5,8 both pass the local distortion constraints.

The desired optimal formation is that which has the least TPD. Using the peak distortion test, the optimal formation for partial path Y8 is determined as:
min[max[Y3$_{TPD}$; peak distortion of cluster 4-8]; max-[Y5$_{TPD}$; peak distortion of cluster 6-8]].

The trace-back pointer would be set to either Y3 or Y5, depending on which formation has the least TPD.

Figure 5D:
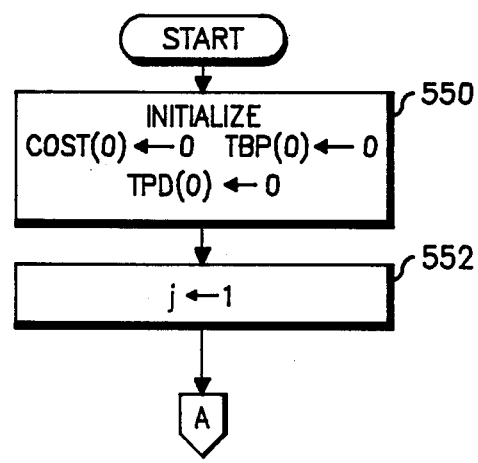

Now referring to FIG. 5d, shown is a flowchart illustrating the formation of partial paths for a sequence of j frames. Discussion of this flowchart pertains to a word template having 4 frames, i.e. N=4. The resulting data reduced template is the same as in the example from FIG. 5b, where $$Y_j = Y1 + C_{1,4}.$$

The null path, partial path Y0, is initialized along with the cost, the traceback pointers and the TPD, block 550. It should be noted that that each partial path has its own set of values for TPD, cost and TBP. A frame pointer, j, is initialized to 1, indicating the first partial path, Y1, block 552. Continuing on to the second part of the flowchart, at FIG. 5e, a second frame pointer, k, is initialized to 0, block 554. The second frame pointer is used to specify how far back frames are considered for clustering in the partial path. Hence, the frames to be considered for clustering are specified from k+1 to j.

These frames are averaged, block 556, and a cluster distortion is generated, block 558. A test is performed to determine if the first cluster of partial path is being formed, block 562. In this instance, the first partial path is being formed. Therefore, the cluster is defined in memory by setting the necessary parameters, block 564. Since this is the first cluster in the first partial path, the traceback pointer (TPD) is set to the null word, the cost is set to 1 and the TPD remains at 0.

The cost for the path ending at frame j is set as the cost of the path ending at j (number of clusters in path j) plus one for the new cluster being added. Testing for a larger cluster formation begins by decrementing the second frame pointer, k, depicted in block 566. At this point, since k is decremented to −1, a test is performed to prevent invalid frame clusters, block 568. A positive result from the test performed at block 568 indicates that all partial paths have been formed and tested for optimality. The first partial path is mathematically defined as Y1=Y0+C0,1. It is comprised of one cluster containing the first frame. The test illustrated in block 570 determines whether all frames have been clustered. There are three frames yet to cluster. The next partial path is initialized by incrementing the first frame pointer j, block 572. The second frame pointer is initialized to one frame before j, block 554. Accordingly, j points to frame 2 and k points to frame 1.

Frame 2 is averaged by itself at block 556. The test performed at block 562 determines that j is equal to k+1 and flow proceeds to block 564 to define the first partial path Y2. The pointer k is decremented at block 566 for the next cluster consideration.

Frames 1 and 2 are averaged to form Y0+C0,2, block 556, and a distortion measure is generated, block 558. Since this is not the first path being formed, block 562, flow proceeds to block 560. The distortion measure is compared to the threshold, block 560. In this example, combining frames 1 and 2 exceeds the threshold. Thus, the previously saved partial path, i.e., Y1+C1,2, is saved for partial path Y2 and the flowchart branches to block 580.

The step depicted in block 580 performs a test to determine whether any additional frames should be clustered with these frames that have exceeded the threshold, block 580. Typically, due to the nature of most data, adding additional frames at this point will also result in an exceeded distortion threshold. However, it has been found that if the generated distortion measure does not exceed the threshold by more than about 20%, additional frames may cluster without exceeding the distortion threshold. If further clustering is desired, the second frame pointer is decremented to specify the new cluster, block 566. Otherwise, the test is performed to indicate whether all frames have been clustered, block 570.

The next partial path is initialized with j set equal to 3, block 572. The second frame pointer is initialized to 2. Frame 3 is averaged by itself, block 556, and a distortion measure is generated, block 558. Since this is the first path formed for Y3, this new path is defined and saved in memory, block 564. The second frame pointer is decremented, block 566, to specify a larger cluster. The larger cluster comprises frames 2 and 3.

These frames are averaged, block 556, and a distortion is generated, block 558. Since this is not the first path formed, block 562, flow proceeds to block 560. In this example, the threshold is not exceeded, block 560. Since this path Y1+C1,3 is more optimal, with two clusters, than path Y2+C2,3 with three clusters, path Y1+C1,3 replaces the previously saved path Y2+C2,3 as partial path Y3. A larger cluster is specified as K is decremented to 0, block 566.

Frames 1 through 3 are averaged, block 556, and another distortion measure is generated, block 558. In this example, the threshold is exceeded, block 560. No additional frames are clustered, block 580, and the test is again performed to determine whether all the frames have been clustered, block 570. Since frame 4 is still not yet clustered, j is incremented for the next partial path, Y4. the second frame pointer is set at frame 3 and the clustering process repeats.

Frame 4 is averaged by itself, block 556. Again, this is the first path formed, in block 562, and the path is defined for Y4, block 564. This partial path Y3+C3,4 has a cost of 3 clusters. A larger cluster is specified, block 566, and frames 3 and 4 are clustered.

Frames 3 and 4 are averaged, block 556. In this example their distortion measure does not exceed the threshold, block 560. This partial path Y2+C2,4 has a cost of 3 clusters. Since this has the same cost as the previous path (Y3+C3,4), flow proceeds thru blocks 574 and 576 to block 578, and the TPD is examined to determine which path has the least distortion. If the current path (Y2+C2,4) has a lower TPD, Block 578, than the current path (Y3+C3,4), then it will replace the current path, block 564 otherwise flow procedes to block 566. A larger cluster is specified, block 566, and frames 2 through 4 are clustered.

Frames 2 through 4 are averaged, block 556. In this example, their distortion measure again does not exceed the threshold. This partial path Y1+C1,4 has a cost of 2 clusters. Since this is a more optimal path for partial path Y4, block 574 than the previous, the path is defined in place of the previous, block 564. A larger cluster is specified, block 566, and frames 1 through 4 are clustered.

Averaging frames 1 through 4, in this example, exceeds the distortion threshold, block 560. Clustering is stopped, block 580. Since all the frames have been clustered, block 570, the stored information defining each cluster defines the optimal path for this 4-frame data reduced word template, block 582, mathematically defined as Y4=Y1+C1,4.

This example illustrates the formation of the optimal data reduced word template from FIG. 3. The flowchart illustrates clustering tests for each partial path in the following order:

| | | | |
|---|---|---|---|
| Y1: | 1 2 3 4 | | |
| Y2: | 1 2 3 4 | *1 2 3 4 | |
| Y3: | 1 2 3 4 | 1 2 3 4 | *1 2 3 4 |

-continued

| Y4: | 1 2 3 <u>4</u> | 1 2 <u>3 4</u> | 1 <u>2 3 4</u> | *<u>1 2 3 4</u> |

The numbers indicating the frame are underlined for each cluster test. Those clusters that exceed the threshold are indicated as such by a preceding '*'.

In this example, 10 cluster paths are searched. In general, using this procedure requires at most [N(N+1)]/2 cluster paths to search for the optimal cluster formation, where N is the number of frames in the word template. For a 15 frame word template, this procedure would require searching at most 120 paths, compared to 16,384 paths for a search attempting to try all possible combinations. Consequently, by using such a procedure in accordance with the present invention, an enormous reduction in computation time is realized.

Figure 5E:
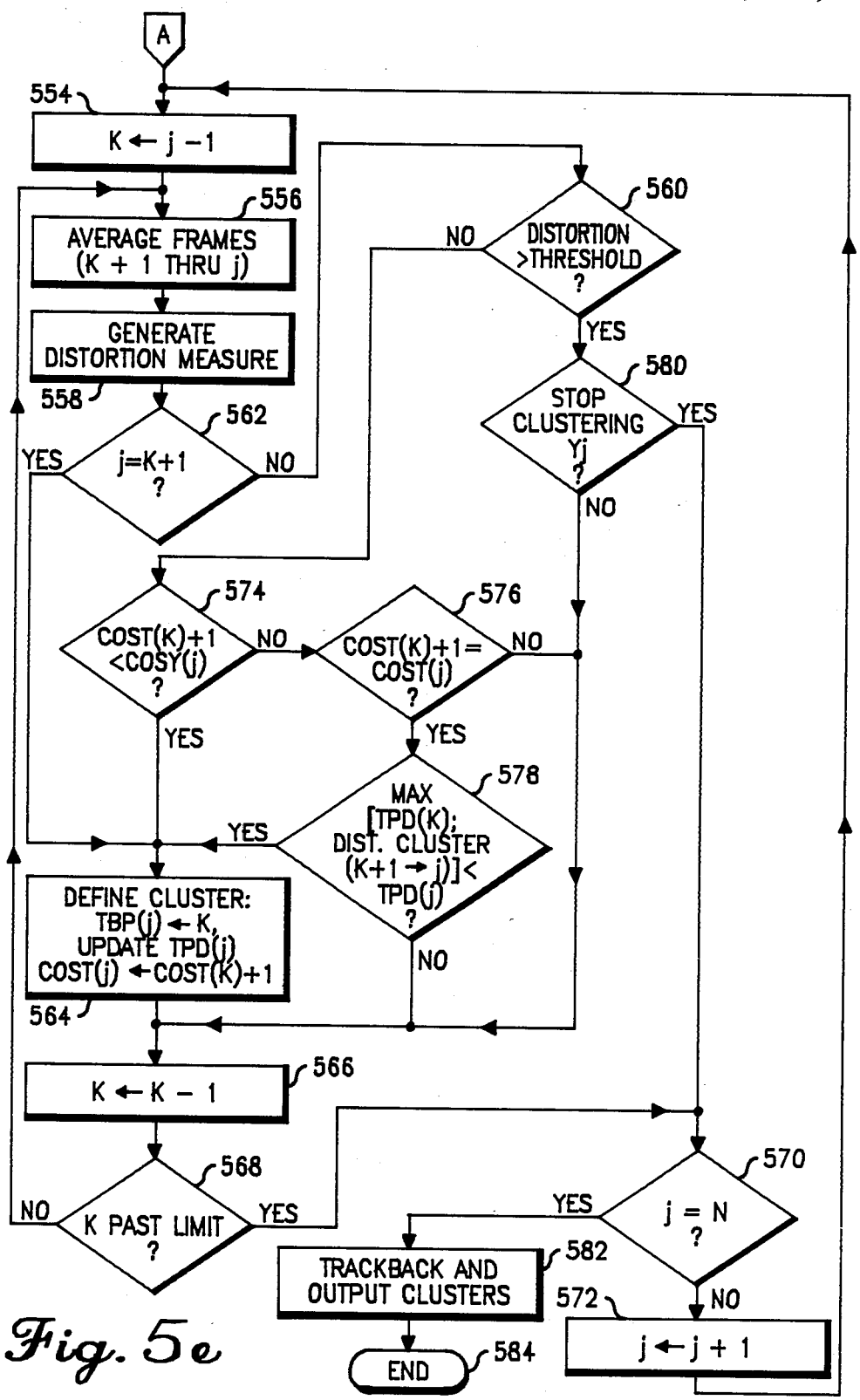

Even further reduction in computation time can be realized by modifying blocks 552, 568, 554, 562, and 580 of FIG. 5e. Block 568 illustrates a limit being placed on the second frame pointer, k. In the example, k is limited only by the null path, partial path Y0, at frame 0. Since k is used to define the length of each cluster, the number of frames clustered can be constrained by constraining k. For any given distortion threshold, there will almost always be a number of frames that, when clustered, will cause a distortion that exceeds the distortion threshold. On the other extreme, there is always a minimal cluster formation that will never cause a distortion that exceeds the distortion threshold. Therefore, by defining a maximum cluster size, MAXCS, and minimum cluster size, MINCS, the second frame pointer, k, can be constrained.

MINCS would be employed in blocks 552, 554 and 562. For block 552, j would be initialized to MINCS. For block 554, rather than subtract one from k in this step, MINCS would be subtracted. This forces k back a certain number of frames for each new partial path. Consequently, clusters with frames less than MINCS will not be averaged. It should also be noted that to accommodate MINCS, block 562 should depict the test of j=k+MINCS rather than j=k+1.

MAXCS would be employed in block 568. The limit becomes either frames before 0 (k<0) or frames before that, designated by MAXCS (k<0-MAXCS). This prevents testing clusters that are known to exceed MAXCS.

According to the notation used with FIG. 5e, these constraints can be mathematically expressed as follows:

k≧j-MAXCS and k≧0; and
k≦j-MINCS and j≧MINCS.

For example, let MAXCS=5 and and MINCS=2 for a partial path Y15. Then the first cluster consists of frames 15 and 14. The last cluster consists of frames 15 through 11. The constraint that j has to be greater or equal to MINCS prevents clusters from forming within the first MINCS frames.

Notice (block 562) that clusters at size MINCS are not tested against the distortion threshold (block 560). This insures that a valid partial path will exist for all yj, j≧MINCS.

By utilizing such constraints in accordance with the present invention, the number of paths that are searched is reduced according to the difference between MAXCS and MINCS.

Figure 5F:
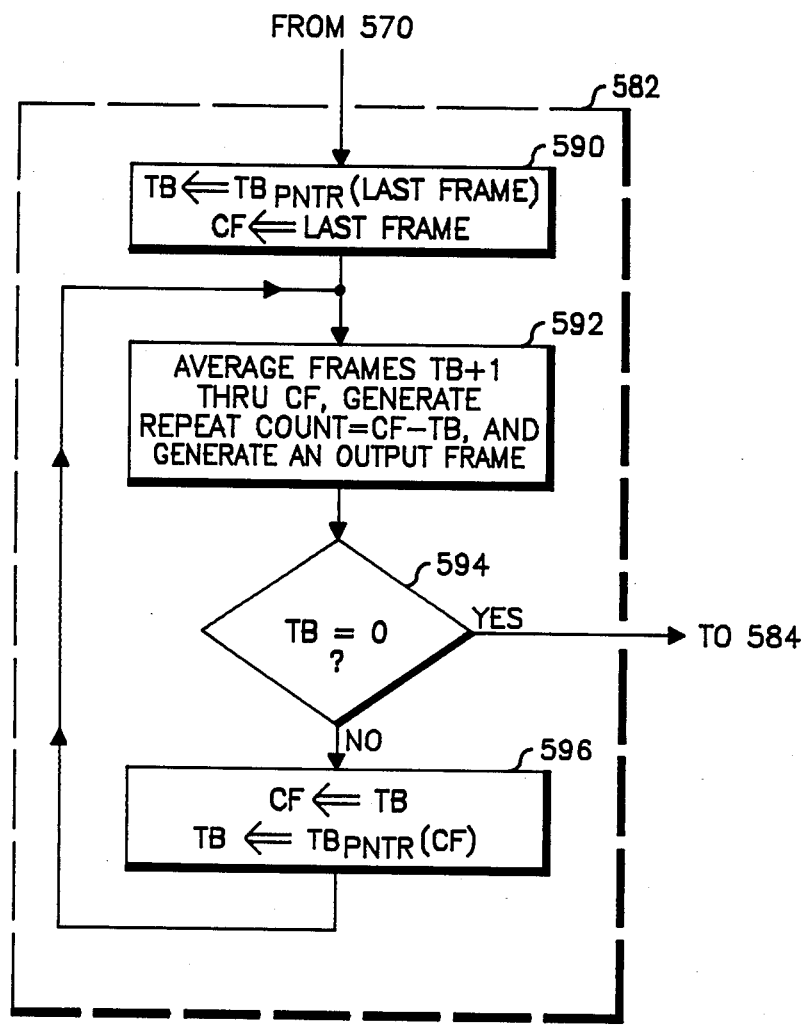
FIG. 5f is a detailed flowchart of the traceback and output clusters block 582 of FIG. 5e, showing the formation of a data reduced word template from previously determined clusters.

Now referring to FIG. 5f, block 582 from FIG. 5e is shown in further detail. FIG. 5f illustrates a method to generate output clusters after data reduction by using the trace back pointer (TBP in block 564 of FIG. 5) from each cluster in reverse direction. Two frame pointers, TB and CF are initialized, block 590. TB is initialized to the trace back pointer of the last frame. CF, the current end frame pointer, is initialized to the last frame of the word template. In the example from FIG. 5d and 5e, TB would point at frame 1 and CF would point at frame 4. Frames TB+1 through CF are averaged to form an output frame for the resulting word template, block 592. A variable for each averaged frame, or cluster, stores the number of frames combined. It is referred to as "repeat count" and can be calculated from CF-TB. See FIG. 6c, infra. A test is then performed to determine whether all clusters have been output, block 594. If not, the next cluster is pointed at by setting CF equal to TB and setting TB to the trace back pointer of new frame CF. This procedure continues until all clusters are averaged and output to form the resultant word template.

FIGS. 5g, 5h and 5i illustrates a unique application of the trace back pointers. The trace back pointers are used in a partial trace back mode for outputting clusters from data with an indefinite number of frames, generally referred to as infinite length data. This is different than the examples illustrated in FIGS. 3 and 5, since those examples used a word template with a finite number of frames, 4.

FIG. 5g illustrates a series of 24 frames, each assigned a trace back pointer defining the partial paths. In this example MINCS has been set to 2 and MAXCS has been set at 5. Applying partial trace back to infinite length data requires that clustered frames be output continuously to define portions of the input data. Hence, by employing the trace back pointers in a scheme of partial trace back, continuous data can be reduced.

FIG. 5h illustrates all partial paths, ending at frames 21-24, converging at frame 10. Frames 1-4, 5-7 and 8-10 were found to be optimal clusters and since the convergence point is frame 10, they can be output.

FIG. 5i shows the remaining tree after frames 1-4, 5-7 and 8-10 have been output. FIGS. 5g and 5h shows the null pointer at frame 0. After the formation of FIG. 5i, the convergence point of frame 10 designates the location of the new null pointer. By tracing back through to the convergence point and outputting frames through that point, infinite length data can be accommodated.

In general, if at frame n, the points to start trace back are n, n-1, n-2, ... n-MAXCS, since these paths are still active and can be combined with more incoming data.

Figure 6A:
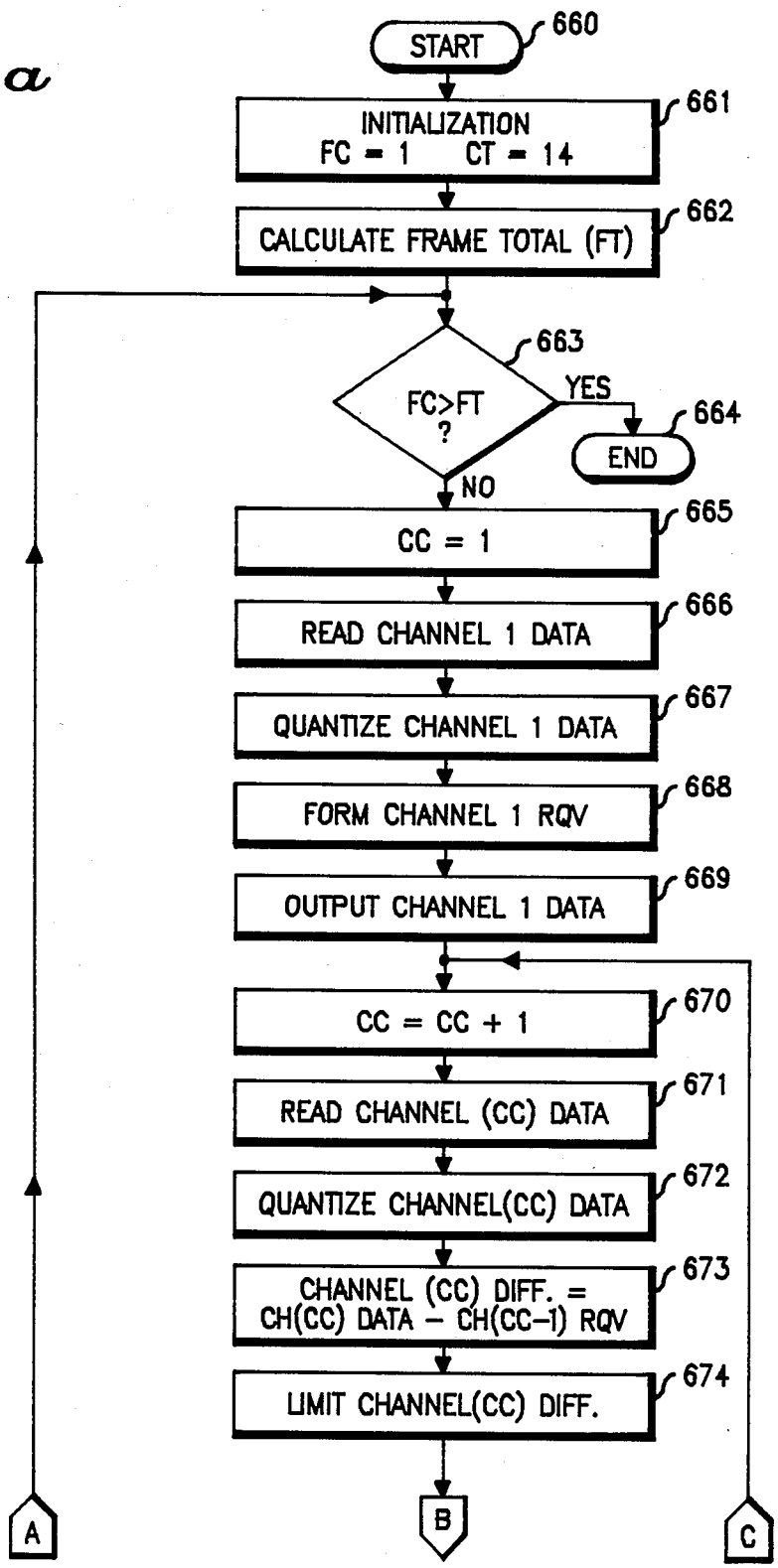
Figure 6B:
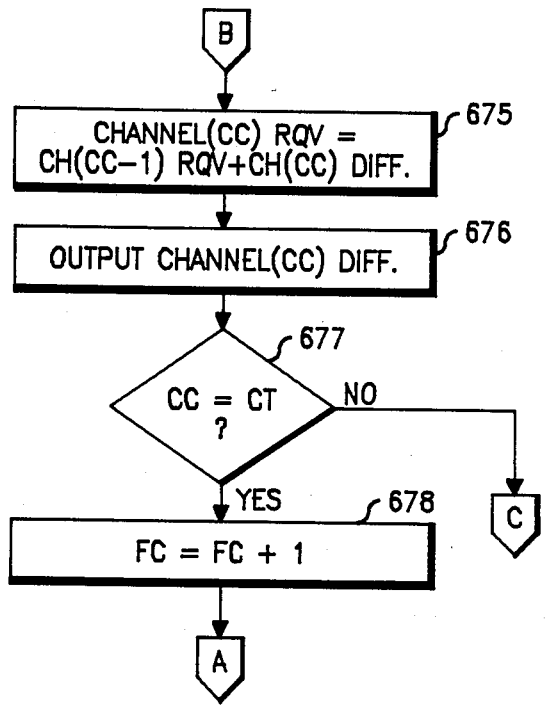
Figure 6C:
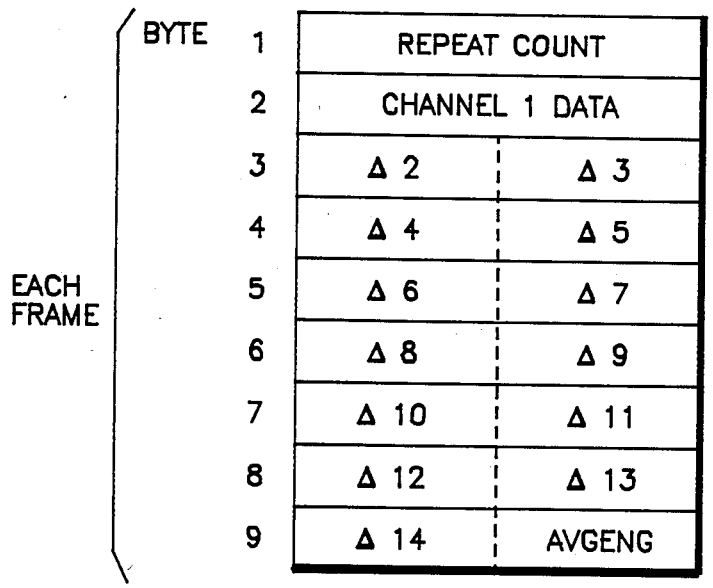
FIG. 6c is a generalized memory map showing the particular data format of one frame of the template memory 160 of FIG. 3.

The flowchart of FIGS. 6a and 6b illustrates the sequence of steps performed by differential encoding block 430 of FIG. 4a. Starting with block 660, the differential encoding process reduces template storage requirements by generating the differences between adjacent channels for storage rather than each channel's actual energy data. The differential encoding process operates on a frame-by-frame basis as described in FIG. 4b. Hence, initialization block 661 sets the frame count FC to one and the channel total CT to 14. Block 662 calculates the frame total FT as before. Block 663 tests to see if all frames of the word have been encoded. If all frames have been processed, the differential encoding ends with block 664.

Block 665 begins the actual differential encoding procedure by setting the channel count CC equal to 1. The energy normalized data for channel one is read into the accumulator in block 666. Block 667 quantizes the channel one data into 1.5 dB steps for reduced storage. The channel data from feature extractor 312 is initially represented as 0.376 dB per step utilizing 8 bits per byte. When quantized into 1.5 dB increments, only 6 bits are required to represent a 96 dB energy range ($2^6 \times 1.5$ dB). The first channel is not differentially encoded so as to form a basis for determining adjacent channel differences.

A significant quantization error could be introduced into the differential encoding process of block 430 if the quantized and limited values of the channel data are not used for calculating the channel differentials. Therefore, an internal variable RQV, the reconstructed quantized value of the channel data is introduced inside the differential encoding loop to take this error into account. Block 668 forms the channel one RQV for later use by simply assigning it a value of the channel one quantized data, since channel one is not differentially encoded. Block 675, discussed below, forms the RQV for the remaining channels. Hence, the quantized channel one data is output (to template memory 160) in block 669.

The channel counter is incremented in block 670, and the next channel data is read into the accumulator at block 671. Block 672 quantizes the energy of this channel data at 1.5 dB per step. Since differential encoding stores the differences between channels rather than the actual channel values, block 673 determines the adjacent channel differences according to the equation:

Channel(CC)differential=CH(CC-)data−CH(CC−1) RQV where CH(CC−1)RQV is the reconstructed quantized value of the previous channel formed in block 675 of the previous loop, or in block 668 for CC=2.

Block 674 limits this channel differential bit value to a −8 to +7 maximum. By restricting the bit value and quantizing the energy value, the range of adjacent channel differences becomes −12 dB/+10.5 dB. Although different applications may require different quantization values or bit limits, our results indicate these values sufficient for our application. Furthermore, since the limited channel difference is a four-bit signed number, two values per byte may be stored. Hence, the limiting and quantization procedures described here substantially reduce the amount of required data storage.

However, if the limited and quantized values of each differential were not used to form the next channel differential, a significant reconstruction error could result. Block 675 takes this error into account by reconstructing each channel differential from quantized and limited data before forming the next channel differential. The internal variable RQV is formed for each channel by the equation:

Channel(CC)RQV=CH(CC−1)RQV+CH(CC-)differential where CH(CC−1)RQV is the reconstructed quantized value of the previous channel differential. Hence, the use of the RQV variable inside the differential encoding loop prevents quantization errors from propagating to subsequent channels.

Block 676 outputs the quantized/limited channel differential to the template memory such that the difference is stored in two values per byte (see FIG. 6c). Block 677 tests to see if all the channels have been encoded. If channels remain, the procedure repeats with block 670. If the channel count CC equals the channel total CT, the frame count FC is incremented in block 678 and tested in block 663 as before.

The following calculations illustrate the reduced data rate that can be achieved with the present invention. Feature extractor 312 generates an 8-bit logarithmic channel energy value for each of the 14 channels, wherein the least significant bit represents three-eights of a dB. Hence, one frame of raw word data applied to data reducer block 322 comprises 14 bytes of data, at 8 bits per byte, at 100 frames per second, which equals 11,200 bits per second.

After the energy normalization and segmentation/compression procedures have been performed, 16 bytes of data per frame are required. (One byte for each of the 14 channels, one byte for the average frame energy AVGENG, and one byte for the repeat count.) Thus, the data rate can be calculated as 16 bytes of data at 8 bits per byte, at 100 frames per second, and assuming an average of 4 frames per repeat count, gives 3200 bits per second.

After the differential encoding process of block 430 is completed, each frame of template memory 160 appears as shown in the reduced data format of FIG. 6c. The repeat count is stored in byte 1. The quantized, energy-normalized channel one data is stored in byte 2. Bytes 3 through 9 have been divided such that two channel differences are stored in each byte. In other words, the differentially encoded channel 2 data is stored in the upper nibble of byte 3, and that of channel 3 is stored in the lower nibble of the same byte. The channel 14 differential is stored in the upper nibble of byte 9, and the average frame energy, AVGENG, is stored in the lower nibble of byte 9. At 9 bytes per frame of data, at 8 bits per byte, at 100 frames per second, and assuming an average repeat count of 4, the data rate now equals 1800 bits per second.

Hence, differential encoding block 430 has reduced 16 bytes of data into 9. If the repeat count values lie between 2 and 15, then the repeat count may also be stored in a four-bit nibble. One may then rearrange the repeat count data format to further reduce storage requirements of 8.5 bytes per frame. Moreover, the data reduction process has also reduced the data rate by at least a factor of six (11,200 to 1800). Consequently, the complexity and storage requirements of the speech recognition system are dramatically reduced, thereby allowing for an increase in speech recognition vocabulary.

3. Decoding Algorithm

Referring to FIG. 7a, shown is an improved word model having frames 720 combined into 3 average frames 722, as discussed with block 420 in FIG. 4a. Each average frame 722 is depicted as a state in a word model. Each state contains one or more substates. The number of substates is dependent on the number of frames combined to form the state. Each substate has an associated distance accumulator for accumulating similarity measures, or distance scores between input frames and the average frames. Implementation of this improved word model is subsequently discussed with FIG. 7b.

Figure 7B:
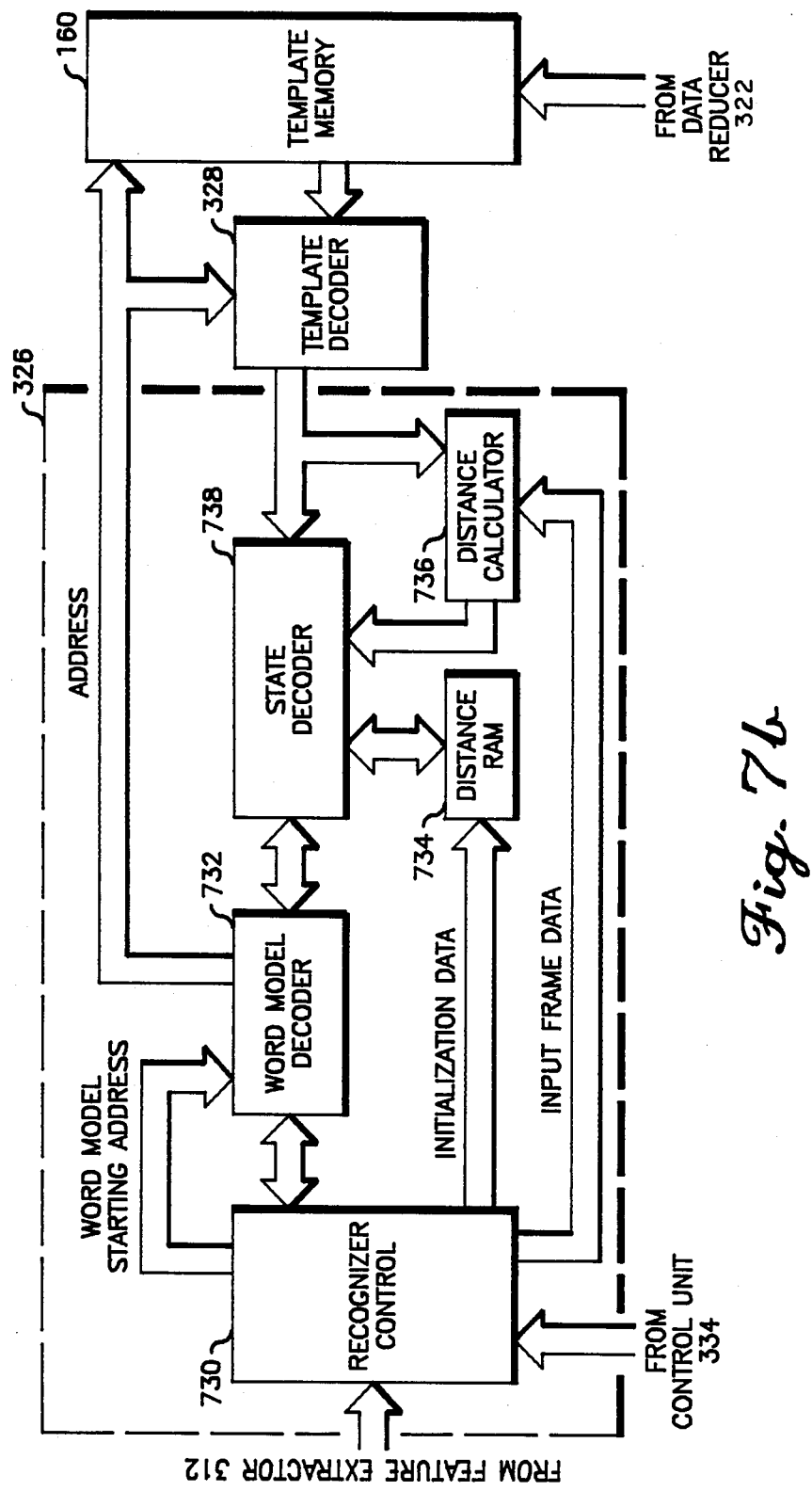
FIG. 7b is a detailed block diagram of the recogition processor 120 of FIG. 3, illustrating its relationship with the template memory 160.

FIG. 7b shows block 120 from FIG. 3 expanded to show specific detail including its relationship with template memory 160. The speech recognizer 326 is expanded to include a recognizer control block 730, a word model decoder 732, a distance ram 734, a distance calculator 736 and a state decoder 738. The template decoder 328 and template memory are discussed immediately following discussion of the speech recognizer 326.

The recognizer control block 730 is used to coordinate the recognition process. Coordination includes endpoint detection (for isolated word recognition), tracking best accumulated distance scores of the word models, maintenance of link tables used to link words (for connected or continuous word recognition), special distance calculations which may be required by a specific recognition process and initializing the distance ram 734. The recognizer control may also buffer data from the acoustic processor. For each frame of input speech, the recognizer updates all active word templates in the template memory. Specific requirements of the recognizer control 730 are discussed by Bridle, Brown and Chamberlain in a paper entitled "An Algorithm for Connected Word Recognition", Proceedings of the 1982 IEEE Int. Conf. on Acoustics, Spedch and Signal Processing, pp. 899–902. A corresponding control processer used by the recognizer control block is described by Peckham, Green, Canning and Stephens in a paper entitled "A Real-Time Hardware Continuos Speech Recognition System", Proceedings of the 1982 IEEE Int. Conf. on Acoustics, Speech and Signal Processing, pp. 863–866.

The distance ram 734 contains accumulated distances used for all substates current to the decoding process. If beam decoding is used, as described by B. Lowerre in "The Harpy Speech Recognition System" Ph.D. Dissertation, Computer Science Dept., Carnegie-Mellon University 1977, then the distance ram 734 would also contain flags to identify which substates are currently active. If a connected word recognition process is used, as described in "An Algorithm for Connected Word Recognition", supra, then the distance ram 734 would also contain a linking pointer for each substate.

The distance calculator 736 calculates the distance between the current input frame and the state being processed. Distances are usually calculated according to the type of feature data used by the system to represent the speech. Bandpass filtered data may use Euclidean or Chebychev distance calculations as described in "The Effects of Selected Signal Processing Techniques on the Performance of a Filter-Bank-Based Isolated Word Recognizer" B. A. Dautrich, L. R, Rabiner, T. B. Martin, Bell System Technical Journal, Vol. 62, No. 5, May-June, 1983 pp. 1311–1336. LPC data may use log-likelihood ratio distance calculation, as described by F. Itakura in "Minimum Prediction Residual Principle Applied to Speech Recognition", IEEE Trans. Acoustics, Speech and Signal Processing, vol. ASSP-23, pp. 67–72, February 1975. The present embodiment uses filtered data, also referred to as channel bank information; hence either Chebychev or Euclidean calculations would be appropriate.

The state decoder 738 updates the distance ram for each currently active state during the processing of the input frame. In other words, for each word model processed by the word model decoder 732, the state decoder 738 updates the required accumulated distances in the distance ram 734. The state decoder also makes use of the distance between the input frame and the current state determined by the distance calculator 736 and, of course, the template memory data representing the current state.

Figure 7C:
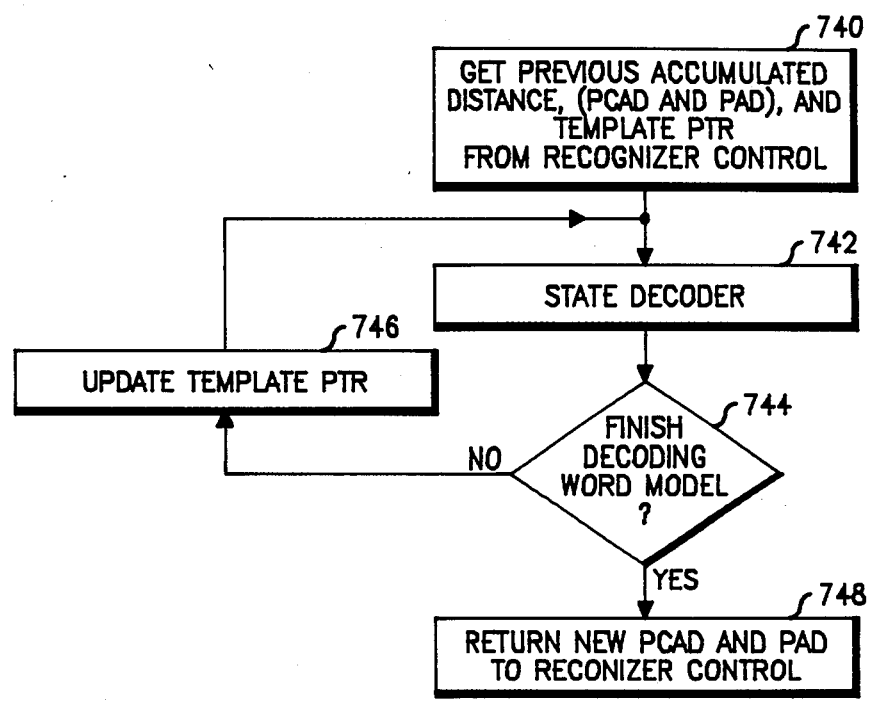
FIG. 7c is a flowchart illustating one embodiment of the sequence of steps required for word decoding according to the present invention.

In FIG. 7c, steps performed by the word model decoder 732, for processing each input frame, are shown in flowchart form. A number of word searching techniques can be used to coordinate the decoding process, including a truncated searching technique, such as Beam Decoding, described by B. Lowerre in "The Harpy Speech Recognition System" Ph.d. Dissertation, Computer Science Dept., Carnegie-Mellon University 1977. It should be noted that implementing a truncated search technique requires the speech recognizer control 730 to keep track of threshold levels and best accumulated distances.

At block 740 of FIG. 7c, three variables are extracted from the recognizer control (block 730 of FIG. 7b). The three variables are PCAD, PAD and Template PTR. Template PTR is used to direct the word model decoder to the correct word template. PCAD represents the accumulated distance from the previous state. This is the distance which is accumulated, exiting from the previous state of the word model, in sequence.

PAD represents the previous accumulated distance, although not necessarily from the previous contiguous state. PAD may differ from PCAD when the previous state has a minimum dwell time of 0, i.e., when the previous state may be skipped all together.

In an isolated word recignition system PAD and PCAD would typically be initialized to 0 by the recognizer control. In a connected or continuous word recognization system the initial values of PAD and PCAD may be determined from outputs of other word models.

In block 742 of FIG. 7c, the state decoder performs the decoding function for the first state of a particular word model. The data representing the state is identified by the Template PTR provided from the recognizer control. The state decoder block is discussed in detail with FIG. 7d.

A test is performed in block 744 to determine if all states of the word model have been decoded. If not, flow returns back to the state decoder, block 742, with an updated Template PTR. If all states of the word model have been decoded, then accmumulated distances, PCAD and PAD, are returned to the recognizer control at block 748. At this point, the recognizer control would typically specify a new word model to decode. Once all word models have been processed it should start processing the next frame of data from the acoustic processor. For an isolated word recognition system when the last frame of input is decoded, PCAD returned by the word model decoder for each word model would represent the total accumulated distance for matching the input utterance to that word model. Typically, the word model with the lowest total accumulated distance would be chosen as the one represented by the utterance which was recognized. Once a template match has been determined, this information is passed to control unit 334.

Figure 7D:
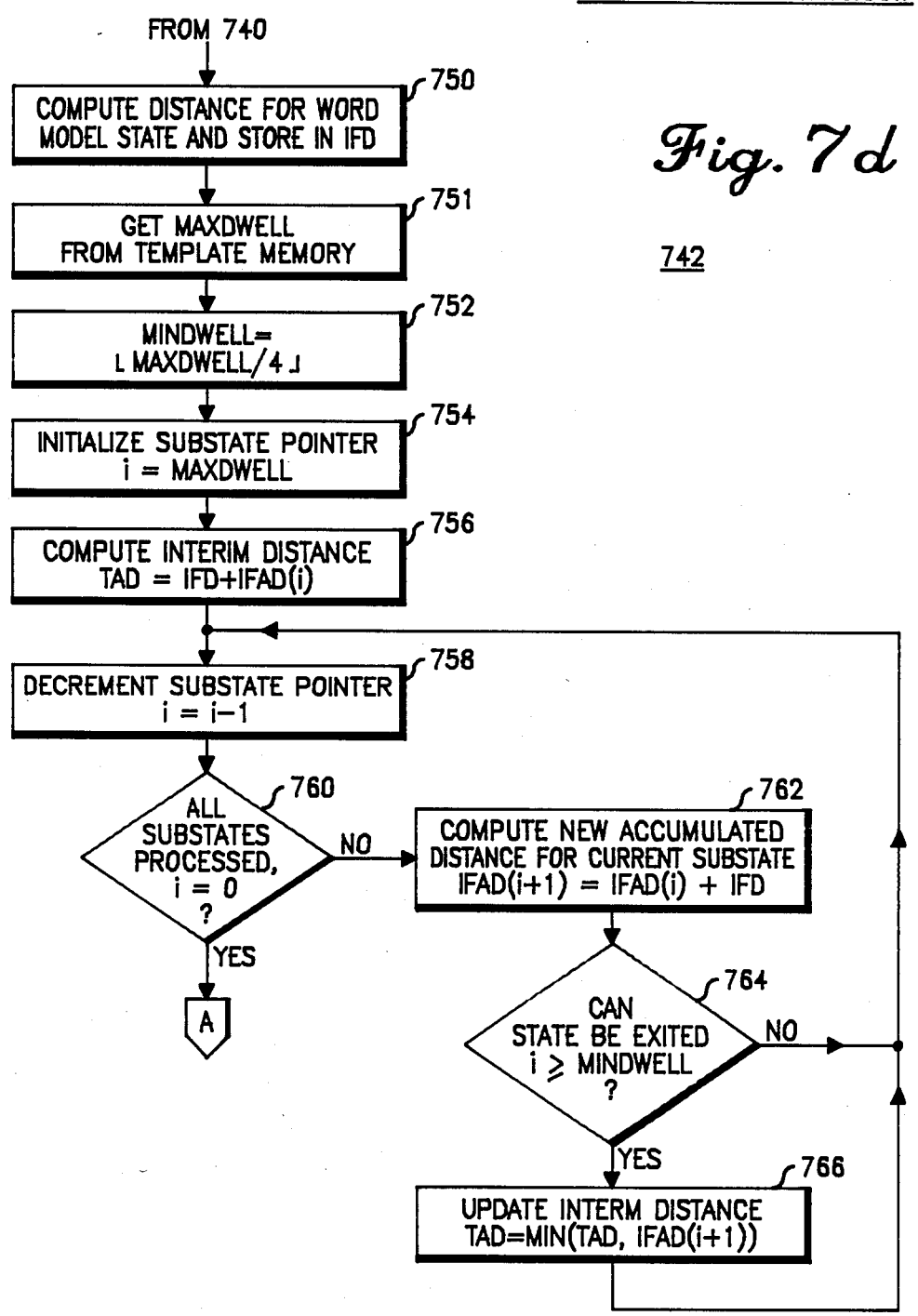
FIGS. 7d and 7e comprise a flowchart illustrating one embodiment of the steps required for state decoding according to the present invention.

Now refering to FIG. 7d, shown is a flowchart for performing the actual state decoding for each state of each word model, i.e., block 742 of FIG. 7c expanded.

The accumulated distances, PCAD and PAD, are passed along to block 750. At block 750, the distance from the word model state to the input frame is computed and stored as a variable called IFD, for input frame distance.

The maxdwell for the state is transferred from template memory, block 751. The maxdwell is determined from the number of frames which are combined in each average frame of the word template and is equivalent to the number of substates in the state. In fact, this system defines the maxdwell as the number of frames which are combined. This is because during word training, the feature extracter (block 310 of FIG. 3) samples the incoming speech at twice the rate it does during the recognition process. Setting maxdwell equal to the number of frames averaged allows a spoken word to be matched to a word model when the word spoken during recognition is up to twice the time length of the word represented by the template.

The mindwell for each state is determined during the state decoding process. Since only the state's maxdwell is passed to the state decoder algorithm, mindwell is calculated as the integer part of maxdwell divided by 4 (block 752). This allows a spoken word to be matched to a word model when the word spoken during recognition is half the time length of the word represented by the template.

A dwell counter, or substate pointer, i, is initialized in block 754 to indicate the current dwell count being processed. Each dwell count is referred to as a substate. The maximum number of substates for each state is defined according to maxdwell, as previously discussed. In this embodiment, the substates are processed in reverse order to facilitate the decoding process. Accordingly, since maxdwell is defined as the total number of substates in the state, "i" is initialy set equal to maxdwell.

In block 756, a temporary accumulated distance, TAD, is set equal to substate i's accumulated distance, referred to as IFAD(i), plus the current input frame distance, IFD. The accumulated distance is presumed to have been updated from the previously processed input frame, and stored in distance ram, block 734 from FIG. 7b. IFAD is set to 0 prior to the initial input frame of the recognition process for all substates of all word models.

The substate pointer is decremented at block 758. If the pointer has not reached 0, block 760, the substate's new accumulated distance, IFAD(i+1), is set equal to the accumulated distance for the previous substate, IFAD(i), plus the current input frame distance, IFD, block 762. Otherwise, flow proceeds to block 768 of FIG. 7e.

A test is performed in block 764, to determine whether the state can be exited from the current substate, i.e. if "i" is greater than or equal to mindwell. Until "i" is less than Mindwell, the temporary accumulated distance, TAD, is updated to the minimum of either the previous TAD or IFAD(i+1), block 766. In other words, TAD is defined as the best accumulated distance leaving the current state.

Figure 7E:
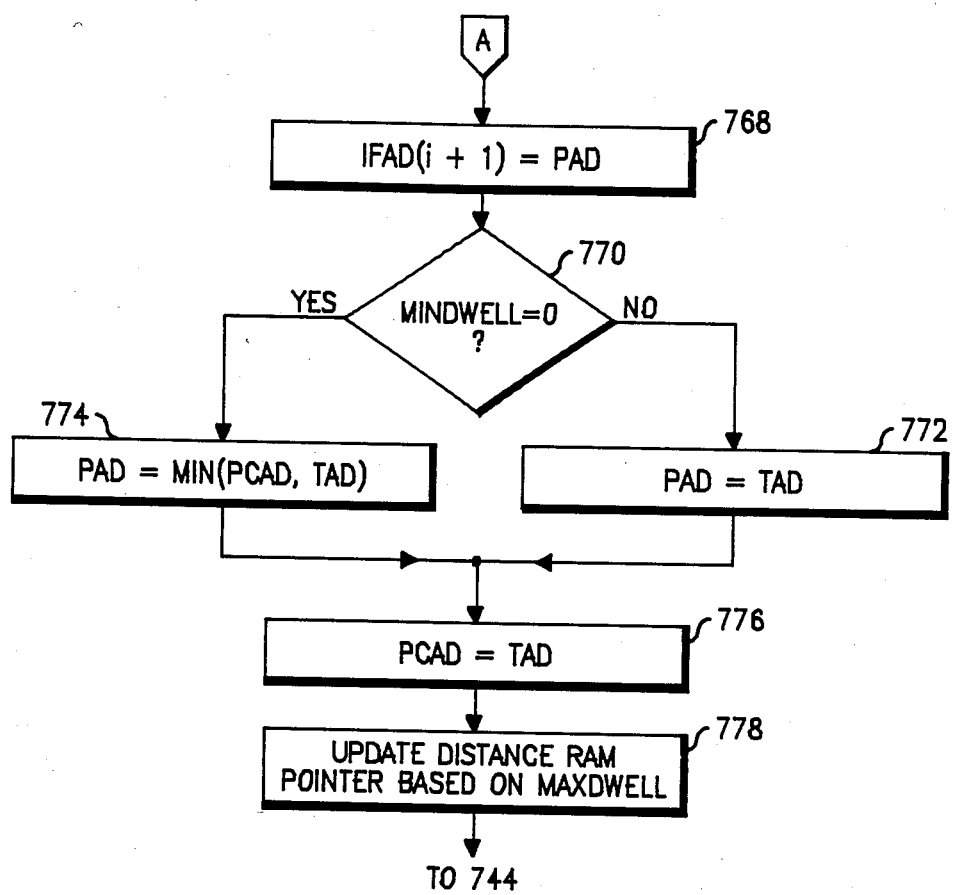

Continuing on to block 768 of FIG. 7e, the accumulated distance for the first substate is set to the best accumulated distance entering the state which is PAD.

A test is then performed to determine if mindwell for the current state is 0, block 770. A mindwell of zero indicates that the current state may be skipped over to yield a more accurate match in the decoding of this word template. If mindwell for the state is not zero, PAD is set equal to the the temporary accumulated distance, TAD, since TAD contains the best accumulated distance out of this state, block 772. If mindwell is zero, PAD is set as the minimum of either the previous state's accumulated distance out, PCAD, or the best accumulated distance out of this state, TAD, block 774. PAD represents the best accumulated distance allowed to enter the next state.

In block 776, the previous contiguous accumulated distance, PAD, is set equal to the best accumulated distance leaving the current state, TAD. This variable is need to complete PAD for the following state if that state has a mindwell of zero. Note, the minimum allowed maxwell is 2, so that 2 adjacent states can never both be skipped.

Finally, the distance ram pointer for the current state is updated to point to the next state in the word model, block 778. This step is required since the substates are decoded from end to beginning for a more efficient algorithm.

The table shown in appendix A illustrates the flowchart of FIGS. 7c, 7d and 7e applied in an example where an input frame is processed through a word model (similar to FIG. 7a) with 3 states, A, B and C. In the example, it is presumed that previous frame have already been processed. Hence, the table includes a column showing "old accumulated distances (IFAD)" for each substate in states A, B and C.

Above the table, information is provided which will be referenced as the example develops. The 3 states have maxdwells of 3, 8 and 4 respectively for A, B and C. The mindwells for each state are shown in the table as 0, 2 and 1 respectively. It should be noted that these have been calculated, according to block 752 of FIG. 7d, as the integer part of Maxdwell/4. Also provided at the top of the table is the input frame distance (IFD) for each state according to block 750 of FIG. 7d. This information could as well have been shown in the table, but it has been excluded to shorten the table and simplify the example. Only pertinent blocks are shown at the left side of the table.

The example begins at block 740 of FIG. 7c. The previous accumulated distances, PCAD and PAD, and the template pointer, which points to the first state of the word template being decoded, are received from the recognizer control. Accordingly, in the first row of the table, state A is recorded along with PCAD and PAD.

Moving onto FIG. 7d, the distance (IFD) is calculated, maxdwell is retrieved from template memory, mindwell is calculated and the substate pointer, "i", is initialized. Only the initialization of the pointer is needed to be shown in the table since maxdwell, mindwell and IFD information is already provided above the table. The second line shows i set equal to 3, the last substate, and the previous accumulated distance is retrieved from the distance ram.

At block 756, the temporary accumulated distance, TAD, is calculated and recorded on the third line of the table.

The test performed at block 760 is not recorded in the table, but the fourth line of the table shows flow moving to block 762 since all substates have not been processed.

The fourth line of the table shows both the decrement of the substate pointer, block 758, and the calculation of the new accumulated distance, block 762. Hence, recorded is i=2, the corresponding old IFAD and the new accumulated distance set at 14, i.e. the previous accumulated distance for the current substate plus the input frame distance for the state.

The test performed at block 764 results in the affirmative. The fifth line of the table shows the temporary accumulated distance, TAD, updated as the minimum of either the current TAD or IFAD(3). In this case, it is the latter, TAD=14.

Flow returns to block 758. The pointer is decremented and the accumulated distance for the second substate is calculated. This is shown on line six.

The first substate is processed similarly, at which point i is detected as equal to 0, and flow proceeds from block 760 to block 768. At block 768, IFAD is set for the first substate according to PAD, the accumulated distance into the current state.

At block 770, the mindwell is tested against zero. If it equals zero, flow proceeds to block 774 where PAD is determined from the minimum of the temporary accumulated distance, TAD, or the previous accumulated distance, PCAD, since the current state can be skipped due to the zero mindwell. Since mindwell=0 for state A PAD is set to mindwell of 9(TAD) and 5(PCAD) which is 5. PCAD is subsequently set equal to TAD, block 776.

Finally, the first state is completely processed with the distance ram pointer updated to the next state in the word model, block 778.

Flow returns to the flowchart in FIG. 7c to update the template pointer and back to FIG. 7d, block 750, for the next state of the word model. This state is processed in a similar manner as the former, with the exceptions that PAD and PCAD, 5 and 9 respectively, are passed from the former state and mindwell for this state is not equal to zero, and block 766 will not be executed for all substates. Hence, block 772 is processed rather than block 774.

The third state of the word model is processed along the same lines as the first and second. After completing the third state, the flowchart of FIG. 7c is returned to with the new PAD and PCAD variables for the recognizer control.

In summary, each state of the word model is updated one substate at a time in reverse order. Two variables are used to carry the most optimal distance from one state to the next. The first, PCAD, carries the minimum accumulated distance from the previous contiguous state. The second variable, PAD, carries the minmum accumulated distance into the current state and is either the minimum accumulated distance out of the previous state (same as PCAD) or if the previous state has a mindwell of 0, the minimum of the minimum accumulated distance out of the previous state and the minimum accumulated distance out of the second previous state. To determine how many substates to process, mindwell and maxdwell are calculated according to the number of frames which have been combined in each state.

The flowcharts of FIGS. 7c, 7d and 7e allow for an optimal decoding of each data reduced word template. By decoding the designated substates in reverse order, processing time is minimized. However, since real time processing requires that each word template must be accessed quickly, a special arrangement is required to readily extract the data reduced word templates.

The template decoder 328 of FIG. 7b is used to extract the specially formatted word templates from the template memory 160 in a high speed fashion. Since each frame is stored in template memory in the differential form of FIG. 6b, the template decoder 328 utilizes a special accessing technique to allow the word model decoder 732 to access the encoded data without excessive overhead.

The word model decoder 732 addresses the template memory 160 to specify the appropriate template to decode. The same information is provided to the template decoder 328, since the address bus is shared by each. The address specifically points to a average frame in the template. Each frame represents a state in the word model. For every state requiring decoding, the address typically changes.

Refering again to the reduced data format of FIG. 6b, once the address of a word template frame is sent out, the template decoder 328 accesses bytes 3 through 9 in a nibble access. Each byte is read as 8-bits and then separated. The lower four bits are placed in a temporary register with sign extension. The upper four bits are shifted to the lower four bits with sign extension and are stored in another temporary register. Each of the differential bytes are retrieved in this manner. The repeat count and the channel one data are retrieved in a normal 8-bit data bus access and temporarily stored in the template decoder 328. The repeat count (maxdwell) is passed directly to the state decoder while the channel one data and channel 2-14 differential data (separated and expanded to 8 bits as just described) are differentially decoded according to the flowchart in FIG. 8b infra before being passed to distance calculator 736.

4. Data Expansion and Speech Synthesis

Referring now to FIG. 8a, a detailed block diagram of data expander 346 of FIG. 3 is illustrated. As will be shown below, data expansion block 346 performs the reciprocal function of data reduction block 322 of FIG. 3. Reduced word data, from template memory 160, is applied to differential decoding block 802. The decoding function performed by block 802 is essentially the inverse algorithm performed by differential encoding block 430 of FIG. 4a. Briefly stated, the differential decoding algorithm of block 802 "unpacks" the reduced word feature data stored in template memory 160 by adding the present channel difference to the previous channel data. This algorithm is fully described in the flowchart of FIG. 8b.

Next, energy denormalization block 804 restores the proper energy contour to the channel data by effecting the inverse algorithm performed in energy normalization block 410 of FIG. 4a. The denormalization procedure adds the average energy value of all channels to each energy-normalized channel value stored in the template. The energy denormalization algorithm of block 804 is fully described in the detailed flowchart of FIG. 8c.

Finally, frame repeating block 806 determines the number of frames compressed into a single frame by segmentation/compression block 420 of FIG. 4a, and performs a frame-repeat function to compensate accordingly. As the flowchart of FIG. 8d illustrates, frame repeating block 806 outputs the same frame data "R" number of times, where R is the prestored repeat count obtained from template memory 160. Hence, reduced word data from the template memory is expanded to form "unpacked" word data which can be interpreted by the speech synthesizer.

Figure 8B:
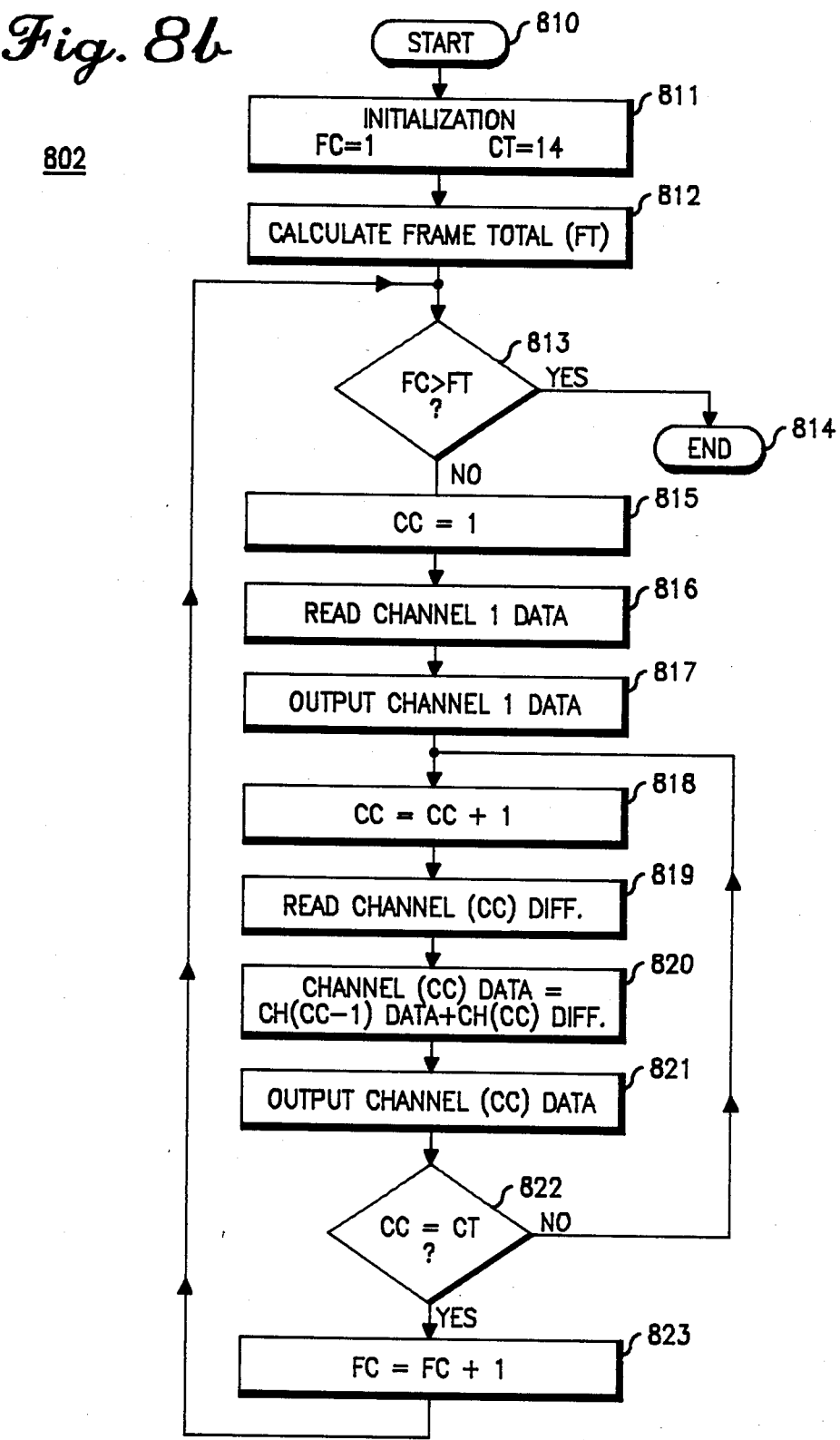

The flowchart of FIG. 8b illustrates the steps performed by differential decoding block 802 of data expander 346. Following start block 810, block 811 initializes the variables to be used in later steps. Frame count FC is initialized to one to correspond to the first frame of the word to be synthesized, and channel total CT is initialized to the total number of channels in the channel-bank synthesizer (14 in the present embodiment).

Next, the frame total FT is calculated in block 812. Frame total FT is the total number of frames in the word obtained from the template memory. Block 813 tests whether all frames of the word have been differentially decoded. If the present frame count FC is greater than the frame total FT, no frames of the word would be left to decode, so that decoding process for that word will end at block 814. If, however, FC is not greater than FT, the differential decoding process continues with the next frame of the word. The test of block 813 may alternatively be performed by checking a data flag (sentinel) stored in the template memory to indicate the end of all channel data.

The actual differential decoding process of each frame begins with block 815. First, the channel count CC is set equal to one in block 815, to determine the channel data to be read first from template memory 160. Next, a full byte of data corresponding to the normalized energy of channel 1 is read from the template in block 816. Since channel 1 data is not differentially encoded, this single channel data may be output (to energy denormalization block 804) immediately via block 817. The channel counter CC is then incremented in block 818 to point to the location of the next channel data. Block 819 reads the differentially encoded channel data (differential) for channel CC into an accumulator. Block 820 then performs the differential decoding function of 820 then performs the differential decoding function of forming channel CC data by adding CC-1 data to the channel CC differential. For example, if CC=2, then the equation of block 820 is:

Channel 2 data=Channel 1 data+Channel 2 Differential.

Block 821 then outputs this channel CC data to energy denormalization block 804 for further processing. Block 822 tests to see whether the present channel count CC is equal to the channel total CT, which would indicate the end of a frame of data. If CC is not equal to CT, then the channel count is incremented in block 818 and the differential decoding process is performed upon the next channel. If all channels have been decoded (when CC equals CT), then the frame count FC is incremented in block 823 and compared in block 813 to perform an end-of-data test. When all frames have been decoded, the differential decoding process of data expander 346 ends at block 814.

Figure 8C:
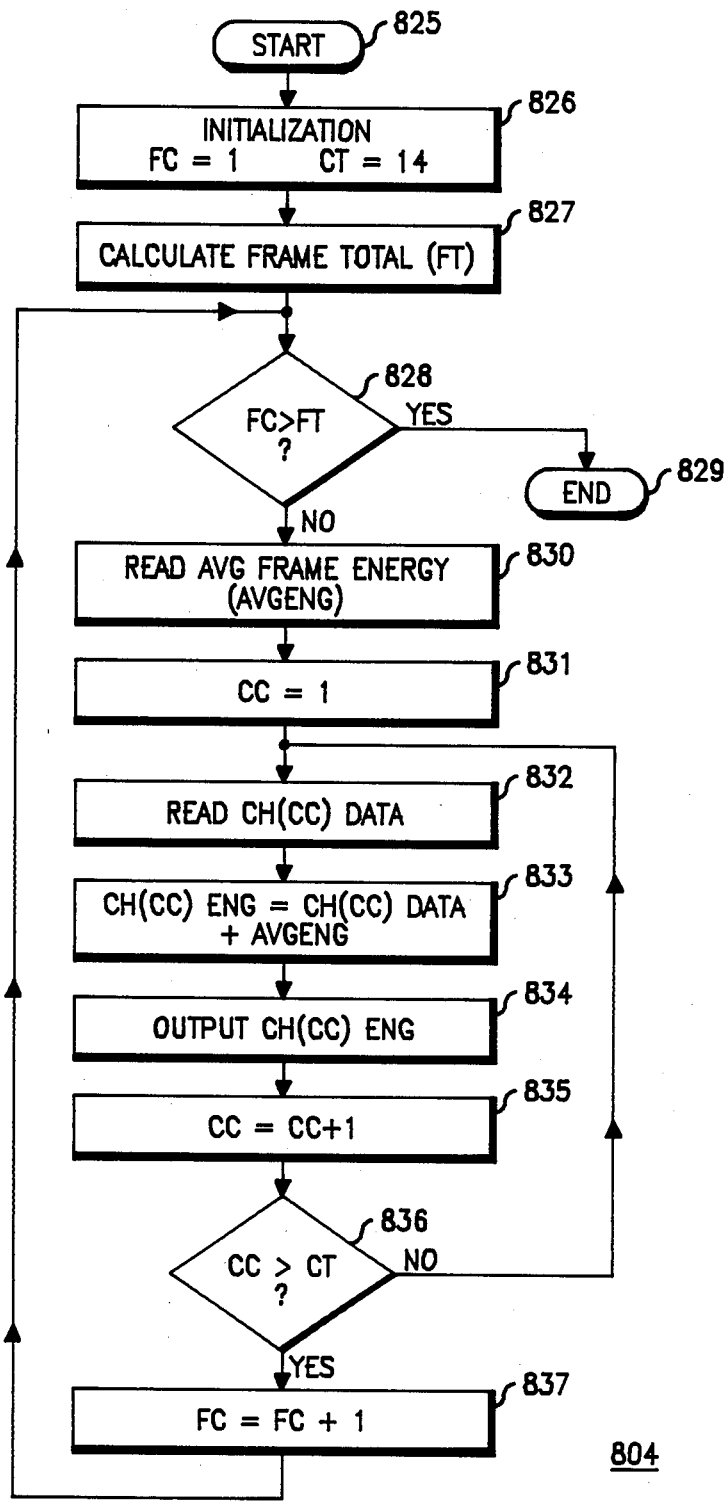
Figure 8D:
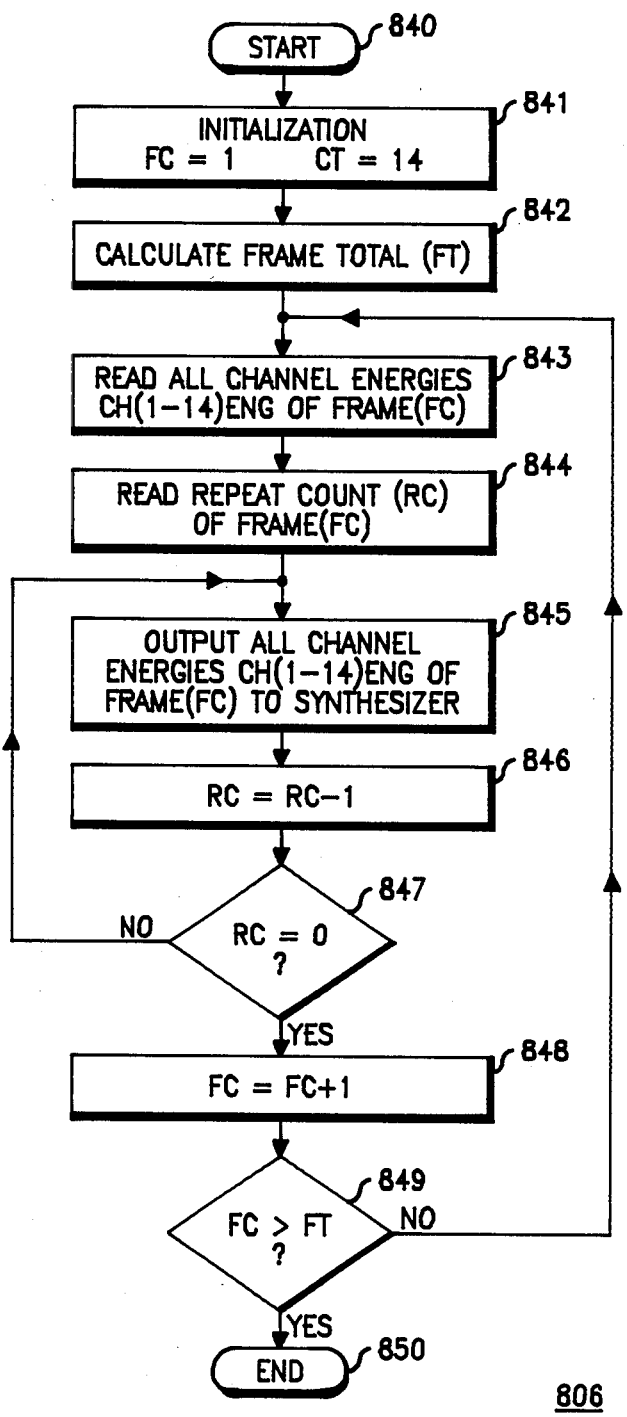

FIG. 8c illustrates the sequence of steps performed by energy denormalization block 804. After starting at block 825, initialization of the variables takes place in block 826. Again, the frame count FC is intitialized to one to correspond to the first frame of the word to be synthesized, and the channel total CT is initialized to the total number of channels in the channel bank synthesizer (14 in this case). The frame total FT is calculated in block 827 and the frame count is tested in block 828, as previously done in blocks 812 and 813. If all frames of the word have been processed (FC greater than FT), the sequence of steps ends at block 829. If, however, frames still need to be processed (FC not greater than FT), then the energy denormalization function is performed.

In block 830, the average frame energy AVGENG is obtained from the template for frame FC. Block 831 then sets the channel count CC equal to one. The channel data, formed from the channel differential in differential decoding block 802 (block 820 of FIG. 8b), is now read in block 832. Since the frame is normalized by subtracting the average energy from each channel in energy normalization block 410 (FIG. 4), it is similarly restored (denormalized) by adding the average energy back to each channel. Hence, the channel is denormalized in block 833 according to the formula shown. If, for example, CC=1, then the equation of block 833 is:

Channel 1 energy=Channel 1 data+average energy.

This denormalized channel energy is then output (to frame repeating block 806) via block 834. The next channel is obtained by incrementing the channel count in block 835, and testing the channel count in block 836 to see if all channels have been denormalized. If all channels have not yet been processed (CC not greater than CT), then the denormalization procedure repeats starting with block 832. If all channels of the frame have been processed (CC greater than CT), then the frame count is incremented in block 837, and tested in block 828 as before. In review, FIG. 8c illustrates how the channel energies are denormalized by adding the average energy back to each channel.

Referring now to FIG. 8d, the sequence of steps performed by frame repeating block 806 of FIG. 8a is illustrated in the flowchart. Again, the process starts at block 840 by first initializing the frame count FC to one and the channel total CT to 14 at block 841. In block 842, the frame total, FT, representing the number of frames in the word, is calculated as before.

Unlike the previous two flowcharts, all channel energies of the frame are simultaneously obtained in block 843, since the individual channel processing has now been completed. Next, the repeat count RC of frame FC is then read from the template data in block 844. This repeat count RC corresponds to the number of frames combined into a single frame from the data compression algorithm performed in segmentation/compression block 420 of FIG. 4. In other words, the RC is the "maxdwell" of each frame. The repeat count is now utilized to output the particular frame "RC" number of times.

Block 845 outputs all the channel energies CH(1-14)ENG of frame FC to the speech synthesizer. This represents the first time the "unpacked" channel energy data is output. The repeat count RC is then decremented by one in block 846. For example, if frame FC was not previously combined, the stored value of RC would equal one, and the decremented value of RC would equal zero. Block 847 then tests the repeat count. If RC is not equal to zero, then the particular frame of channel energies is again output in block 845. RC would again be decremented in block 846, and again tested in block 847. When RC is decremented to zero, the next frame of channel data is obtained. Thus, the repeat count RC represents the number of times the same frame is output to the synthesizer.

To obtain the next frame, the frame count FC is incremented in block 848, and tested in block 849. If all the frames of the word have been processed, the sequence of steps corresponding to frame repeating block 806 ends at block 850. If more frames need to be processed, the frame repeating function continues with block 843.

As we have seen, data expander block 346 essentially performs the inverse function of "unpacking" the stored template data which has been "packed" by data reduction block 322. It is to be noted that the separate functions of blocks 802, 804, and 806 may also be performed on a frame-by-frame basis, instead of the word-by-word basis illustrated in the flowcharts of FIGS. 8b, 8c, and 8d. In either case, it is the combination of data reduction, reduced template format, and data expansion techniques which allows the present invention to synthesize intelligible speech from speech recognition templates at a low data rate.

As illustrated in FIG. 3, both the "template" word voice reply data, provided by data expander block 346, and the "canned" word voice reply data, provided by reply memory 344, are applied to channel back speech synthesizer 340. Speech synthesizer 340 selects one of these data sources in response to a command signal from control unit 334. Both data sources 344 and 346 contain prestored acoustic feature information corresponding to the word to be synthesized.

This acoustic feature information comprises a plurality of channel gain values (channel energies), each representative of the acoustic energy in a specified frequency bandwidth, corresponding to the bandwidths of feature extractor 312. There is, however, no provision in the reduced template memory format to store other speech synthesizer parameters such as voicing or pitch information. This is due to the fact that voicing and pitch information is not normally provided to speech recognition processor 120. Therefore, this information is usually not retained primarily to reduce template memory requirements. Depending on the particular hardware configuration, reply memory 344 may or may not provide voicing and pitch information. The following channel bank synthesizer description assumes that voicing and pitch information are not stored in either memory. Hence, channel bank speech synthesizer 340 must synthesize words from a data source which is absent voicing and pitch information. One important aspect of the present invention directly addresses this problem.

Figure 9A:
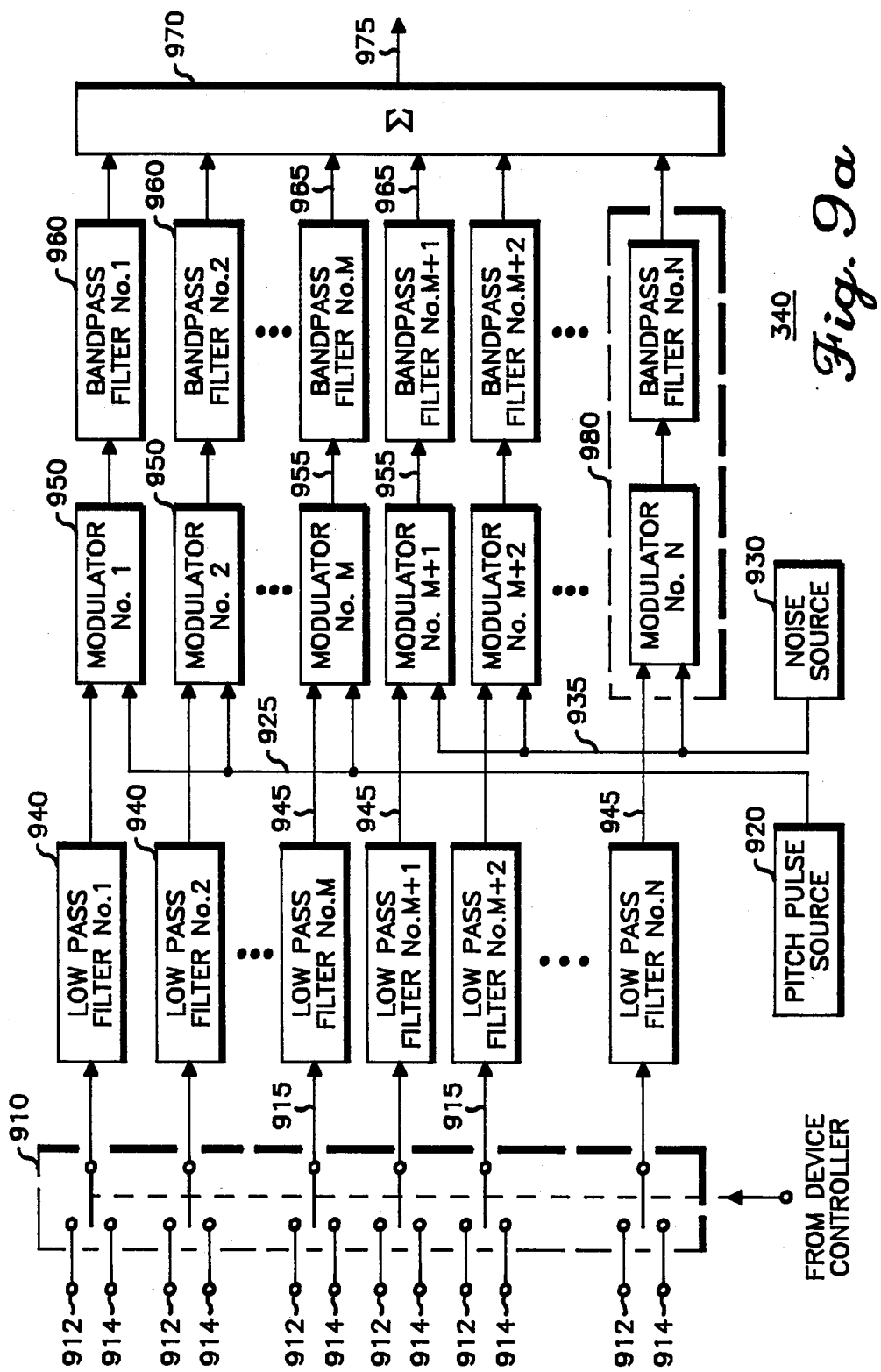
FIG. 9a is a detailed block diagram of the channel bank speech synthesizer 340 of FIG. 3.

FIG. 9a illustrates a detailed block diagram of channel bank speech synthesizer 340 having N channels. Channel data inputs 912 and 914 represent the channel data outputs of reply memory 344 and data expander 346, respectively. Accordingly, switch array 910 represents the "data source decision" provided by device controller unit 334. For example, if a "canned" word is to be synthesized, channel data inputs 912 from reply memory 344 are selected as channel gain values 915. If a template word is to be synthesized, channel data inputs 914 from data expander 346 are selected. In either case, channel gain values 915 are routed to low-pass filters 940.

Low-pass filters 940 function to smooth the step discontinuities in frame-to-frame channel gain changes before feeding them to the modulators. These gain smoothing filters are typically configured as second-order Butterworth lowpass filters. In the present embodiment, lowpass filters 940 have a −3 dB cutoff frequency of approximately 28 Hz.

Smoothed channel gain values 945 are then applied to channel gain modulators 950. The modulators serve to adjust the gain of an excitation signal in response to the appropriate channel gain value. In the present embodiment, modulators 950 are divided into two predetermined groups: a first predetermined group (numered 1 through M) having a first excitation signal input; and a second group of modulators (numbered M+1 through N) having a second excitation signal input. As can be seen from FIG. 9a, the first excitation signal 925 is output from pitch pulse source 920, and the second excitation signal 935 is output from noise source 930. These excitation sources will be described in further detail in the following figures.

Speech synthesizer 340 employs the technique called "split voicing" in accordance with the present invention. This technique allows the speech synthesizer to reconstruct speech from externally-generated acoustic feature information, such as channel gain values 915, without using external voicing information. The preferred embodiment does not utilize a voicing switch to distinguish between the pitch pulse source (voiced excitation) and the noise source (unvoiced excitation) to generate a single voiced/unvoiced excitation signal to the modulators. In contrast, the present invention "splits" the acoustic feature information provided by the channel gain values into two predetermined groups. The first predetermined group, usually corresponding to the low frequency channels, modulates the voiced excitation signal 925. A second predetermined group of channel gain values, normally corresponding to the high frequency channels, modulates the unvoiced excitation signal 935. Together, the low frequency and high frequency channel gain values are individually bandpass filtered and combined to generate a high quality speech signal.

It has been found that a "9/5 split" (M=9) for a 14-channel synthesizer (N=14) has provided excellent results for improving the quality of speech. However, it will be apparent to those skilled in the art that the voiced/unvoiced channel "split" can be varied to maximize the voice quality characteristics in particular synthesizer applications.

Modulators 1 through N serve to amplitude modulate the appropriate excitation signal in response to the acoustic feature information of that particular channel. In other words, the pitch pulse (buzz) or noise (hiss) excitation signal for channel M is multiplied by the channel gain value for channel M. The amplitude modification performed by modulators 950 can readily be implemented in software using digital signal processing (DSP) techniques. Similarly, modulators 950 may be implemented by analog linear multipliers as known in the art.

Both groups of modulated excitation signals 955 (1 through M, and M+1 through N) are then applied to bandpass filters 960 to reconstruct the N speech channels. As previously noted, the present embodiment utilizes 14 channels covering the frequency range 250 Hz to 3400 Hz. Additionally, the preferred embodiment utilizes DSP techniques to digitally implement in software the function of bandpass filters 960. Appropriate DSP algorithms are described in chapter 11 of L. R. Rabiner and B. Gold, Theory and Application of Digital Signal Processing, (Prentice Hall, Englewood Cliffs, N.J., 1975).

The filtered channel outputs 965 are then combined at summation circuit 970. Again, the summing function of the channel combiner may be implemented either in software, using DSP techniques, or in hardware, utilizing a summation circuit, to combine the N channels into a single reconstructed speech signal 975.

Figure 9B:
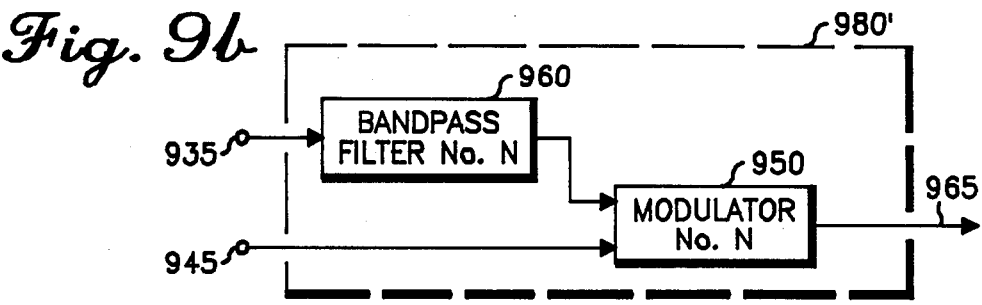

An alternate embodiment of the modulator/bandpass filter configuration 980 is shown in FIG. 9b. This figure illustrates that it is functionally equivalent to first apply excitation signal 935 (or 925) to bandpass filter 960, and then amplitude modulate the filtered excitation signal by channel gain value 945 in modulator 950. This alternate configuration 980' produces the equivalent channel output 965, since the function of reconstructing the channels is still achieved.

Noise source 930 produces unvoiced excitation signal 935, called "hiss". The noise source output is typically a series of random amplitude pulses of a constant average power, as illustrated by waveform 935 of FIG. 9d. Conversely, pitch pulse source 920 generates a pulse train of voiced excitation pitch pulses, also of a constant average power, called "buzz". A typical pitch pulse source would have its pitch pulse rate determined by an external pitch period $f_0$. This pitch period information, determined from an acoustic analysis of the desired synthesizer speech signal, is normally transmitted along with the channel gain information in a vocoder application, or would be stored, along with the voiced/unvoiced decision and channel gain information, in a "canned" word memory. However, as noted above, there is no provision in the reduced template memory format of the preferred embodiment to store all of these speech synthesizer parameters, since they are not all required for speech recognition. Hence, another aspect of the present invention is directed toward providing a high quality synthesized speech signal without prestored pitch information.

Figure 9C:
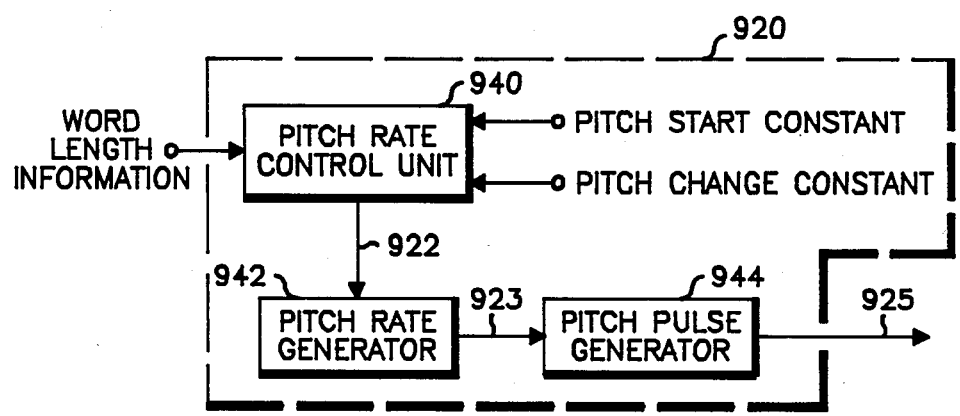

Pitch pulse source 920 of the preferred embodiment is shown in greater detail in FIG. 9c. It has been found that a significant improvement in synthesized voice quality can be achieved by varying the pitch pulse period such that the pitch pulse rate decreases over the length of the word synthesized. Therefore, excitation signal 925 is preferably comprised of pitch pulses of a constant average power and of a predetermined variable rate. This variable rate is determined as a function of the length of the word to be synthesized, and as a function of empirically-determined constant pitch rate changes. In the present embodiment, the pitch pulse rate linearly decreases on a frame-by-frame basis over the length of the word. However, in other applications, a different variable rate may be desired to produce other speech sound characteristics.

Referring now to FIG. 9c, pitch pulse source 920 is comprised of pitch rate control unit 940, pitch rate generator 942, and pitch pulse generator 944. Pitch rate control unit 940 determines the variable rate at which the pitch period is changed. In the preferred embodiment, the pitch rate decrease is determined from a pitch change constant, initialized from a pitch start constant, to provide pitch period information 922. The function of pitch rate control unit 940 may be performed in hardware by a programmable ramp generator, or in software by the controlling microcomputer. The operation of control unit 940 is fully described in conjunction with the next figure.

Pitch rate generator 942 utilizes this pitch period information to generate pitch rate signal 923 at regularly spaced intervals. This signal may be impulses, rising edges, or any other type of pitch pulse period conveying signal. Pitch rate generator 942 may be a timer, a counter, or crystal clock oscillator which provides a pulse train equal to pitch period information 922. Again, in the present embodiment, the function of pitch rate generator 942 is performed in software.

Pitch rate signal 923 is used by pitch pulse generator 944 to create the desired waveform for pitch pulse excitation signal 925. Pitch pulse generator 944 may be a hardware waveshaping circuit, a monoshot clocked by pitch rate signal 923, or, as in the present embodiment, a ROM look-up table having the desired waveform information. Excitation signal 925 may exhibit the waveform of impulses, a chirp (frequency swept sine wave) or any other broadband waveform. Hence, the nature of the pulse is dependent upon the particular excitation signal desired.

Since excitation signal 925 must be of a constant average power, pitch pulse generator 944 also utilizes the pitch rate signal 923, or the pitch period 922, as an amplitude control signal. The amplitude of the pitch pulses are scaled by a factor proportional to the square root of the pitch period to obtain a constant average power. Again, the actual amplitude of each pulse is dependent upon the nature of the desired excitation signal.

Figure 9D:
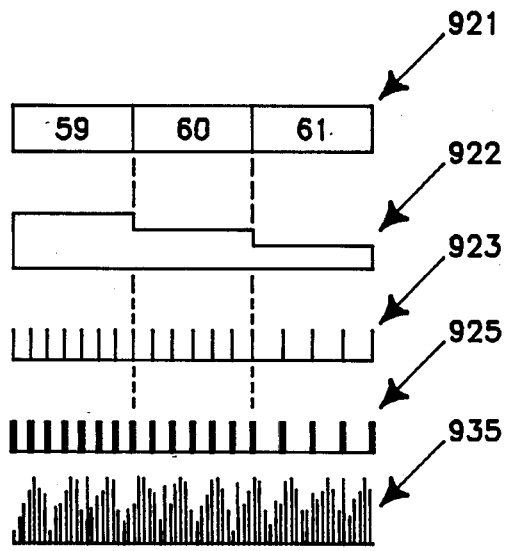
FIG. 9d is a graphic representation illustrating various waveforms of FIGS. 9a and 9c.

The following discussion of FIG. 9d, as applied to pitch pulse source 920 of FIG. 9c, describes the sequence of steps taken in the preferred embodiment to produce the variable pitch pulse rate. First, the word length WL for the particular word to be synthesized is read from the template memory. This word length is the total number of frames of the word to be synthesized. In the preferred embodiment, WL is the sum of all repeat counts for all frames of the word template. Second, the pitch start constant PSC and pitch change constant PCC are read from a predetermined memory location in the synthesizer controller. Third, the number of word divisions are calculated by dividing the word length WL by the pitch change constant PCC. The word division WD indicates how many consecutive frames will have the same pitch value. For example, waveform 921 illustrates a word length of 3 frames, a pitch start constant of 59, and a pitch change constant of 3. Thus, the word division, in this simple example, is calculated by dividing the word length (3) by the pitch change constant (3), to set the number of frames between pitch changes equal to one. A more complicated example would be if WL=24 and PCC=4, then the word divisions would occur every 6 frames.

The pitch start constant of 59 represents the number of sample times between pitch pulses. For example, at an 8 kHz sampling rate, there would be 59 sample times (each 125 microseconds in duration) between pitch pulses. Therefore, the pitch period would be 59×125 microseconds=7.375 milliseconds or 135.6 Hz. After each word division, the pitch start constant is incremented by one (i.e. 60=133.3 Hz, 61=131.1 Hz) such that the pitch rate decreases over the length of the word. If the word length was longer, or the pitch change constant was shorter, several consecutive frames would have the same pitch value. This pitch period information is represented in FIG. 9d by waveform 922. As waveform 922 illustrates, the pitch information may be represented in a hardware sense by changing voltage levels, or in software by different pitch period values.

When pitch period information 922 is applied to pitch rate generator 942, pitch rate signal waveform 923 is produced. Waveform 923 generally illustrates, in a simplified manner, that the pitch rate is decreasing at a rate determined by the variable pitch period. When the pitch rate signal 923 is applied to pitch pulse generator 944, excitation waveform 925 is produced. Waveform 925 is simply a waveshaped variation of waveform 923 having a constant average power. Waveform 935, representing the output of noise source 930 (hiss), illustrates the difference between periodic voiced and random unvoiced excitation signals.

As we have seen, the present invention provides a method and apparatus for synthesizing speech without voicing or pitch information. The speech synthesizer of the present invention employs the technique of "split voicing" and the technique of varying the pitch pulse period such that the pitch pulse rate decreases over the length of the word. Although either technique may be used by itself, the combination of split voicing and variable pitch pulse rate allows natural-sounding speech to be generated without external voicing or pitch information.

While specific embodiments of the present invention have been shown and described herein, further modifications and improvements may be made by those skilled in the art. All such modifications which retain the basic underlying principles disclosed and claimed herein are within the scope of this invention.

said template, said processing method comprising the steps of:
(a) combining contiguous acoustically similar frames of a previous frame set into representative frames to form a reduced template;
(b) storing said reduced template in template memory; and
(c) comparing frames of said given frame set to said representative frames of said reduced template according to the number of frames combined in said representative frames of said reduced template to produce a measure of similarity between the given frame set and the template.

2. The method of claim 1, wherein combining further includes the steps of generating a distortion measure for each representative frame and comparing each said distortion measure to a predetermined distortion threshold.

APPENDIX A

Processing of one input frame for 3 states of a word model, states A, B and C.
State A: Maxdwell = 3, Mindwell = 0 (752-FIG. 7(d)), IFD = 7 (750-FIG. 7(d))
State B: Maxdwell = 8, Mindwell = 2 (752-FIG. 7(d)), IFD = 3 (750-FIG. 7(d))
State C: Maxdwell = 4, Mindwell = 1 (752-FIG. 7(d)), IFD = 5 (750-FIG. 7(d))

| BLK/FIG. | State/Substate | IN PAD | IN PCAD | OUT PAD | OUT PCAD | Old IFAD(i) (Given) | NEW IFAD(i + 1) | TAD |
|---|---|---|---|---|---|---|---|---|
| 740/7(c) | A | 5 | 5 | | | | | |
| 754/7(d) 756 | i = 3 | | | | | $8_{(3)}$ | | |
| 758,762 766 | i = 2 | | | | | $7_{(2)}$ | $14_{(3)} = 7 + 7$ | $15 = 7 + 8$ |
| 758,762 766 | i = 1 | | | | | $2_{(1)}$ | $9_{(2)} = 2 + 7$ | 14 |
| 758 768 | i = 0 | | | | | | | 9 |
| 774,776 778 | | | | 5 | 9 | | $5_{(1)}$ | |
| 754 756 | B | 5 | 9 | | | $5_{(8)}$ | | |
| | i = 8 | | | | | | | |
| 758,762 766 | i = 7 | | | | | $9_{(7)}$ | $12_{(8)} = 9 + 3$ | $8 = 3 + 5$ |
| 758,762 766 | i = 6 | | | | | $3_{(6)}$ | $6_{(7)} = 3 + 3$ | 8 8 |
| 758,762 766 | i = 5 | | | | | $8_{(5)}$ | $11_{(6)} = 8 + 3$ | 6 |
| 758,762 766 | i = 4 | | | | | $4_{(4)}$ | $7_{(5)} = 4 + 3$ | 6 |
| 758,762 766 | i = 3 | | | | | $4_{(3)}$ | $7_{(4)} = 4 + 3$ | |
| 758,762 766 | i = 2 | | | | | $5_{(2)}$ | $8_{(3)} = 5 + 3$ | 6 |
| 758,762 766 | i = 1 | | | | | $2_{(1)}$ | $5_{(2)} = 2 + 3$ | 6 |
| 758 768 | i = 0 | | | | | | | 6 |
| 772,776 778 | | 6 | 6 | 6 | 6 | | $5_{(1)}$ | |
| 754 756 | i = 4 | | | | | $10_{(4)}$ | | |
| 758,762 766 | i = 3 | | | | | $8_{(3)}$ | $13_{(4)} = 8 + 5$ | $15 = 5 + 10$ |
| 758,762 766 | i = 2 | | | | | $6_{(2)}$ | $11_{(3)} = 6 + 5$ | 13 |
| 758,762 766 | i = 1 | | | | | $9_{(1)}$ | $14_{(2)} = 9 + 5$ | 11 |
| 758 768 | i = 0 | | | | | | | 11 |
| 772,776 778 | | | | 11 | 11 | | $6_{(1)}$ | |
| 744/7(c) 748 | | 11 | 11 | | | | | |

What is claimed is:

1. A method for processing speech information in a speech recognition system, wherein the information is represented by a sequence of frames, said speech recognition system being capable of comparing a given frame set to a template, and having template memory to store old.

3. The method of claim 1, wherein combining further includes the step of determining a distortion measure corresponding to said reduced template.

4. The method of claim 1, further including the step of determining the number of frames combined in each representative frame.

5. The method of claim 1, wherein storing further includes the step of storing the number of frames combined into each representative frame.

6. The method of claim 1, further including the step of determining the number of representative frames representing said reduced template.

7. The method of claim 1, wherein storing further includes the step of storing a first element of frame data corresponding to the difference between a second element of frame data and said first element of frame data.

8. The method of claim 1, wherein storing further includes the step of storing an energy measure for each representative frame.

9. The method of claim 1, wherein comparing further includes the step of accumulating distance measures corresponding to the difference between the given input word and the reduced template.

10. A method for generating a measure of similarity for speech information in a speech recognition system, wherein the information is represented by a sequence of frames, said speech recognition system being capable of comparing a given input frame set to a template, said method comprising the steps of:
    combining contiguous acoustically similar frames of a previous frame set into representative frames to form a reduced template;
    comparing frames of said given frame set to said representative frames of said reduced template by accumulating a set of distance measures for each representative frame, each said set having a total number of accumulated distance measures corresponding to the number of frames combined in each said representative frame; and
    determining a measure of similarity between said given frame set and said template based on said accumulated distance measures.

11. The method of claim 10, wherein comparing further includes the step of defining a maximum number of accumulations for a particular representative frame corresponding to the number of frames combined into said particular representative frame.

12. The method of claim 11, wherein comparing further includes the step of defining a minimum number of accumulations proportional to said maximum number of accumulations for said particular representative frame.

13. The method of claim 10, wherein comparing further includes the step of sequentially accumulating similarity measures corresponding to two representative frames, two said representative frames being separated by at least one other said representative frame, but without accumulating a similarity measure from said other representative frame.

14. An arrangement for processing speech information in a speech recognition system, wherein the information is represented by a sequence of frames, said speech recognition system being capable of comparing a given frame set to a template, and having template memory to store said template, said processing arrangement comprising:
    (a) means for combining contiguous acoustically similar frames of a previous frame set into representative frames to form a reduced template;
    (b) means for storing said reduced template in template memory; and
    (c) means for comparing frames of said given frame set to said representative frames of said reduced template according to the number of frames combined in said representative frames of said reduced template to produce a measure of similarity between the given frame set and the template.

15. The arrangement of claim 1, wherein means for combining further includes means for generating a distortion measure for each representative frame and comparing each said distortion measure to a predetermined distortion threshold.

16. The arrangement of claim 1, wherein means for combining further includes means for determining a distortion measure corresponding to said reduced template.

17. The arrangement of claim 1, further including means for determining the number of frames combined in each representative frame.

18. The arrangement of claim 1, wherein means for storing further includes means for storing the number of frames combined into each representative frame.

19. The arrangement of claim 1, further including means for determining the number of representative frames representing said reduced template.

20. The arrangement of claim 1, wherein means for storing further includes means for storing a first element of frame data corresponding to the difference between a second element of frame data and said first element of frame data.

21. The arrangement of claim 1, wherein means for storing further including means for storing an energy measure for each representative frame.

22. The arrangement of claim 1, wherein means for comparing further includes means for accumulating distance measures corresponding to the difference between the given input word and the reduced template.

23. An arrangement for generating a measure of similarity for speech information in a speech recognition system, wherein the information is represented by a sequence of frames, said speech recognition system being capable of comparing a given input frame set to a template, said arrangement comprising:
    means for combining contiguous acoustically similar frames of a previous frame set into representative frames to form a reduced template;
    means for comparing frames of said given frame set to said representative frames of said reduced template by accumulating a set of distance measures for each representative frame, each said set having a total number of accumulated distance measures corresponding to the number of frames combined in each said representative frame; and
    means for determining a measure of similarity between said given frame set and said template based on said accumulated distance measures.

24. The arrangement of claim 10, wherein means for comparing further includes means for defining a maximum number of accumulations for a particular representative frame corresponding to the number of frames combined into said particular representative frame.

25. The arrangement of claim 11, wherein means for comparing further includes means for defining a minimum number of accumulations proportional to said maximum number of accumulations for said particular representative frame.

26. The arrangement of claim 10, wherein means for comparing further includes means for sequentially accumulating similarity measures corresponding to two representative frames, two said representative frames being separated by at least one other said representative frame, but without accumulating a similarity measure from said other representative frame.

27. The method for processing speech information in a speech recognition system, wherein the information is represented by a sequence of frames, said speech recognition system being capable of comparing a given frame-set to a template using a word model comprising of a plurality of states, and having template memory to store said template, said processing method comprising the steps of:
  (a) combining contiguous acoustically similar frames of a previous frame-set into representative frames;
  (b) forming a word model having a plurality of states, each state corresponding to one of said representative frames; and
  (c) comparing at least a predetermined minimum number of frames of the given frame-set to a state of the word model according to the number of frames combined in said representative frames to produce a measure of similarity between the given frame-set and the template.

28. The method for processing speech information in a speech recognition system, wherein the information is represented by a sequence of frames, said speech recognition system being capable of comparing a given frame-set to a template using a word model comprising of a plurality of states, and having template memory to store said template, said processing method comprising the steps of:
  (a) combining contiguous acoustically similar frames of a previous frame-set into representative frames;
  (b) forming a word model having a plurality of states, each state corresponding to one of said representative frames; and
  (c) comparing not more than a predetermined maximum number or frames of the given frame-set to a state of the word model according to the number of frames combined in said representative frames to produce a measure of similarity between the given frame-set and the template.

29. The method for processing speech information in a speech recognition system, wherein the information is represented by a sequence of frames, said speech recognition system being capable of comparing a given frame-set to a template using a word model comprising of a plurality of states, and having template memory to store said template, said processing method comprising the steps of:
  (a) combining contiguous acoustically similar frames of a previous frame-set into representative frames;
  (b) forming a word model having a plurality of states, each state corresponding to one of said representative frames; and
  (c) comparing at least a predetermined minimum number of frames, but not more than a predetermined maximum number of frames, of the given frame-set to a state of the word model according to the number of frames combined in said representative frames to produce a measure of similarity between the given frame-set and the template.

* * * * *